United States Patent
Williams et al.

(10) Patent No.: US 6,178,355 B1
(45) Date of Patent: Jan. 23, 2001

(54) INTRACARDIAC DEFIBRILLATION LEADS

(75) Inventors: Terrell M. Williams, Brooklyn Park; Peter M. J. Mulier, Stillwater; John G. Keimel, New Brighton; Timothy G. Laske, Shoreview; Gregory A. Boser, Richfield; Mary M. Morris, Moundsview; Xiaoyi Min, Plymouth, all of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/216,293

(22) Filed: Dec. 18, 1998

Related U.S. Application Data

(62) Division of application No. 09/062,373, filed on Apr. 17, 1998, now Pat. No. 5,871,530, which is a division of application No. 08/840,691, filed on Apr. 29, 1997.

(51) Int. Cl.[7] .................................................. A61N 1/05
(52) U.S. Cl. ................................................................ 607/122
(58) Field of Search ................................ 607/119, 122, 607/123, 126, 127

(56) References Cited

U.S. PATENT DOCUMENTS

| | | |
|---|---|---|
| 3,729,008 | 4/1973 | Berkovits . |
| 4,106,512 | 8/1978 | Bisping . |
| 4,161,952 | 7/1979 | Kinney et al. . |
| 4,332,259 * | 6/1982 | McCorkle, Jr. ................ 607/123 |
| 4,355,646 | 10/1982 | Kallok et al. . |
| 4,402,330 | 9/1983 | Lindemans . |
| 4,414,983 | 11/1983 | Dickhurdt et al. . |
| 4,481,953 | 11/1984 | Gold et al. . |
| 4,708,145 | 11/1987 | Tacker, Jr. et al. . |
| 4,735,205 | 4/1988 | Chachques et al. . |
| 4,934,049 | 6/1990 | Kiekhafer et al. . |
| 4,951,687 | 8/1990 | Ufford et al. . |
| 4,953,551 | 9/1990 | Mehra et al. . |
| 4,998,975 | 3/1991 | Cohen et al. . |
| 5,007,436 | 4/1991 | Smits . |
| 5,010,894 | 4/1991 | Edhag . |
| 5,042,143 | 8/1991 | Holleman et al. . |
| 5,044,374 | 9/1991 | Lindemans et al. . |
| 5,050,601 | 9/1991 | Kupersmith et al. . |
| 5,099,838 | 3/1992 | Bardy . |
| 5,107,834 | 4/1992 | Ideker et al. . |
| 5,111,811 | 5/1992 | Smits . |
| 5,111,830 | 5/1992 | Bemurat . |
| 5,133,365 | 7/1992 | Heil, Jr. et al. . |
| 5,143,089 | 9/1992 | Alt . |
| 5,144,960 | 9/1992 | Mehra et al. . |
| 5,165,403 | 11/1992 | Mehra . |
| 5,170,802 | 12/1992 | Mehra . |
| 5,174,288 | 12/1992 | Bardy et al. . |
| 5,224,491 | 7/1993 | Mehra . |
| 5,246,014 | 9/1993 | Williams et al. . |
| 5,257,634 | 11/1993 | Kroll . |
| 5,303,704 | 4/1994 | Molacek et al. . |
| 5,312,355 | 5/1994 | Lee . |
| 5,607,385 | 3/1997 | Franciscelli et al. . |
| 5,908,446 * | 6/1999 | Imran ................................ 607/122 |

* cited by examiner

*Primary Examiner*—William E. Kamm
(74) *Attorney, Agent, or Firm*—Reed A. Duthler; Harold R. Patton

(57) ABSTRACT

A lead and a lead system for dispersion of a cardioversion/defibrillation electrode formed of one or more small diameter defibrillation electrodes in a heart chamber and for attaching a pace/sense electrode in contact with the heart. The small diameter defibrillation electrode or electrodes extend distally from the distal end of the lead body. If multiple electrodes are employed, they are preferably biased to spread apart when unrestrained and have a cross-section size small enough to be inserted into interstices of trabeculae in the ventricular chamber. The distal ends of the defibrillation electrodes may be free of attachment to the lead body or may be attached by a weak bond to the distal portion of the lead.

13 Claims, 20 Drawing Sheets

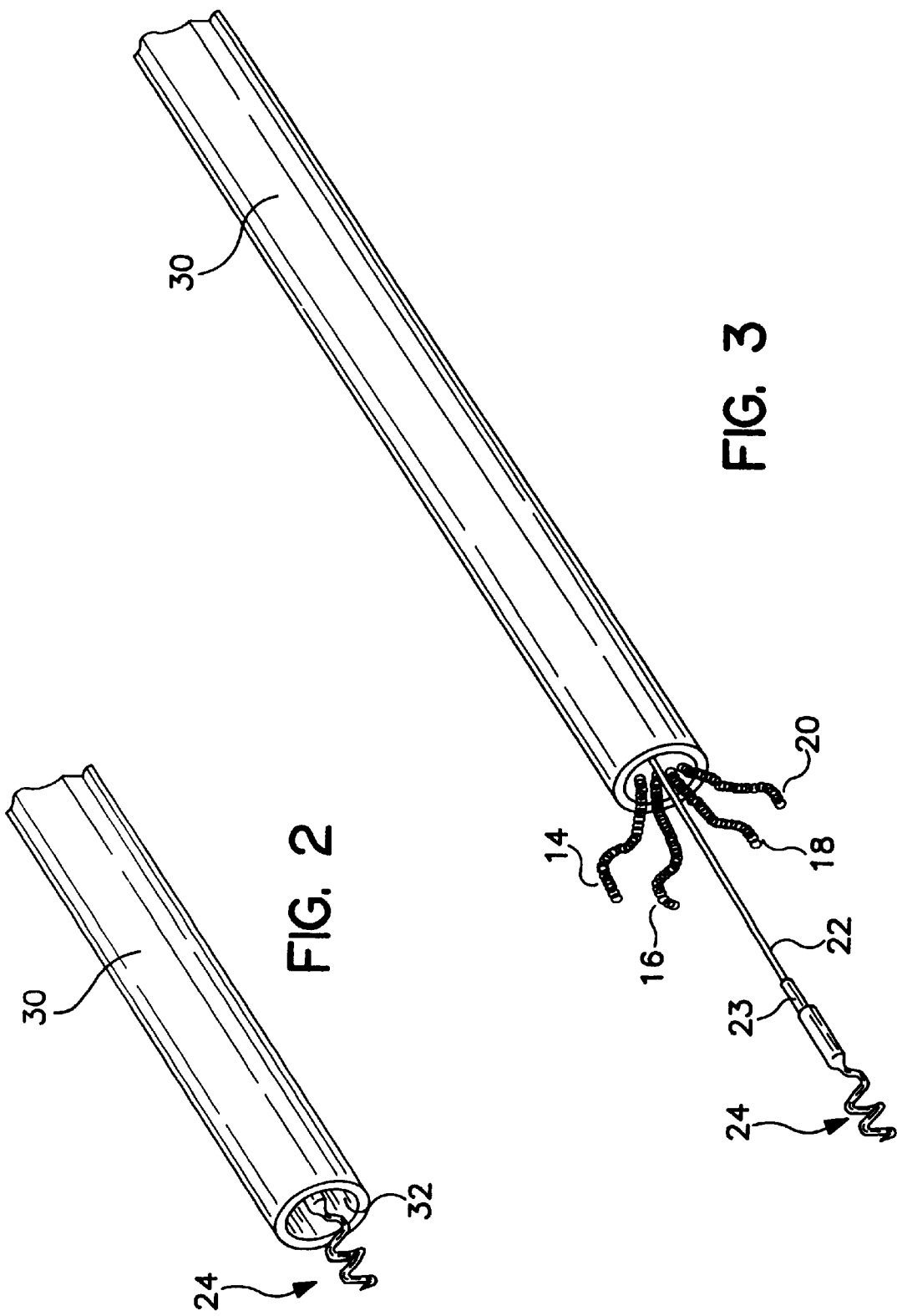

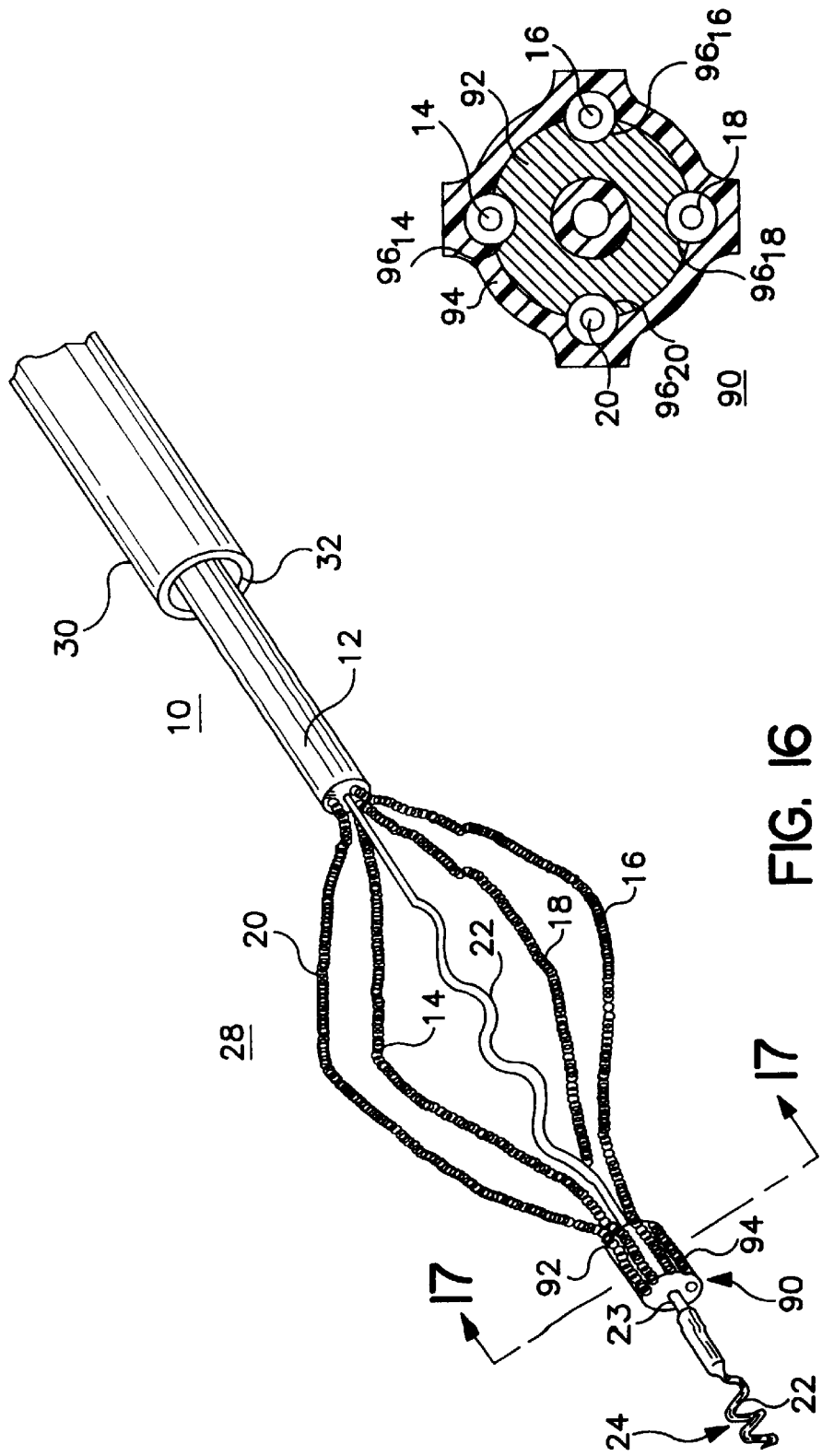

INTRACARDIAC DEFIBRILLATION LEADS

This application is a division of application Ser. No. 09/062,373 filed Apr. 17, 1998, now U.S. Pat. No. 5,871, 530, which is a divisional application of Ser. No. 08/840,691 filed Apr. 29, 1997.

FIELD OF THE INVENTION

The present invention relates to medical stimulators and leads generally, and more particularly to implantable bradyarrhythmia and tachyarrhythmia leads, particularly intracardiac cardioversion/defibrillation leads having one or more small diameter elongated defibrillation electrodes.

BACKGROUND OF THE INVENTION

In the design of implantable defibrillation electrodes, it has traditionally been understood to be desirable to achieve a low impedance to the delivered current of the defibrillation pulse by employing low resistance materials, providing as large an electrode area as is practical for the implant site, and distributing that surface area over an even larger area. Early attempts to employ large diameter, endocardial leads bearing elongated, surface mounted, right ventricular electrodes showed that the necessary low impedance to allow use with implantable defibrillators was not possible to obtain. As a result, early automatic implantable cardioverter/ defibrillators used large surface area, epicardial defibrillation patch electrodes that conformed to surface areas of the heart. However, the stress, pain and expense of the required thoracotomy to position the electrodes gave incentive to the development of the wide variety of endocardial defibrillation leads.

More recently, improvements in electrode materials and lead construction, the delivered shock waveforms and electrode combinations for optimal cardioversion pathways have allowed the clinical use of intracardiac electrodes in the right ventricle and/or right atrium.

One difficulty in achieving large surface area, distributed electrodes within the right ventricle (and the right atrium) lies in the physical constraints presented by the chamber itself. A further difficulty lies in the desire to make the lead body as small as possible to make the implantation easier. In addition, it is desired that the same lead carry the pace/sense unipolar or bipolar electrode(s) and a fixation mechanism to provide intimate contact of at least the distal pace/sense electrode with cardiac tissue. A further requirement is that there be no possibility whatsoever that the defibrillation electrode and the pace/sense electrode(s) contact one another. Finally, it is highly desirable or required that the lead be removable from the heart chamber after chronic use and consequent fibrosis of the lead.

Currently available implantable ventricular defibrillators typically employ epicardial or subcutaneous patch electrodes, alone, or in conjunction with one or more endocardial leads with one or more electrodes disposed within a heart chamber or blood vessel. Other contemplated multi-lead and multi-electrode atrial and/or ventricular defibrillation systems are widely disclosed, as exemplified in U.S. Pat. Nos. 4,708,145 to Tacker, et al., 4,998,975 to Cohen et al., 5,007,436 to Smits, 5,099,838 to Bardy, 5,107,834 to Ideker et al, 5,111,811 to Smits, 5,165,403 to Mehra, and 5,174,288 to Bardy et al.

Ventricular defibrillation is typically effected with at least one electrode disposed within the right ventricle extending along the length of the endocardial lead body and one or more electrodes disposed outside the right ventricle. Many versions of right ventricular defibrillation electrodes have been disclosed in the above listed patents and in further single endocardial lead systems as shown, for example, in further U.S. Pat. Nos. 4,481,953 to Gold et al., 4,161,952 to Kinney, et al., 4,934,049 to Kiekhafer et al., 5,010,894 to Edhag, 5,042,143 to Holleman, et al., 5,050,601 to Kupersmith et al., 5,133,365 to Heil, Jr. et al., and 5,144,960 to Mehra et al.

The positioning of at least a portion of the right ventricular (RV) lead electrode in proximity to the septum of the heart is considered to be desirable. In the above-referenced U.S. Pat. No. 4,998,975, 5,007,436, 5,111,811, 5,107,834 and 5,010,894, U-shaped RV defibrillation leads are described and depicted which have at least a distal portion of the elongated defibrillation electrode shaped to bear against the septum. A U-shaped loop biased into the apex of the right ventricle is relied on to provide the force to press the distal portion back proximally along the septum. These RV leads either have a single or multiple defibrillation electrodes spaced along the lead body. In the U.S. Pat. No. 5,107,834, the distal end of the lead bears a separate electrode that is intended to be directed into the outflow tract while more proximally located RV and RA/SVC electrodes are positioned in the right ventricle and the right atrium or superior vena cava, respectively.

In leads of this type, it is necessary to employ a separate endocardial lead having a distal pace/sense electrode that is wedged deep into the apex of the right ventricle or to rely on a ring shaped electrode as shown in the U.S. Pat. No. 5,107,834. In the lead of the U.S. Pat. No. 5,107,834, it is not possible to obtain the deep apical positioning of the pace/ sense RV ring electrode, and pacing is compromised by the poor contact with myocardial cells. In the endocardial leads shown in the U.S. Pat. Nos. 5,010,894 and 4,998,975, additional RV lead structures are disclosed that employ active or passive fixations mechanisms for fixing the RV pace sense electrodes on the lead bodies. A pair of RV defibrillation electrodes are formed on bifurcations of the lead body or in free legs that extend back from the point of attachment in the apex of the right ventricle. The disclosed lead system of the U.S. Pat. No. 4,998,975 otherwise includes epicardial electrodes positioned in a radical endocardial approach involving perforating the inferior vena cava wall.

The bifurcated and U-shaped lead bodies depicted in the U.S. Pat. No. 4,998,975, for example, encounter a significant difficulty in effecting removal after chronic implantation. The fibrotic reaction encases the lead and electrode surfaces and grows through the bifurcation or inside the U-shape, rendering removal through traction very difficult if not impossible.

It is proposed in U.S. Pat. No. 5,257,634 to Kroll that the elongated electrode extending along the lead body be provided with relatively short conductor extensions that spring outward from the elongated electrode when the introducer catheter is withdrawn after placement of the electrode in the desired chamber. The conductor extensions only extend a short distance and effectively only increase the effective diameter of the electrode body and do not disperse the electrode surface over a wide area or volume.

In a further U.S. Pat. No. 5,143,089 to Alt, an epicardial lead is described having a distal electrode formed of a brush-like arrangement of fine, electrically conductive, carbonized polymer fibers to achieve high flexibility and distribution of the electrode surface area over a relatively large area. The electrode is introduced through the pericardium to a position adjacent the epicardium. The carbonized polymer fibers may break away. While this may not lead to any complications in the pericardial sac, the breakage and loss of such fibers could not be tolerated within the blood stream. The pace/sense electrode(s) are included on a RV endocardial lead so that the electrodes cannot short out on contact with the carbonized polymer fibers.

Despite these improvements, the achievement of appreciably lower cardioversion/defibrillation thresholds with current lead systems employing endocardial RV and RA electrodes continues to be a goal.

SUMMARY OF THE INVENTION

It is therefore an object of the present invention to provide a cardioversion/defibrillation and pace/sense lead for intra-atrial or intra-ventricular implantation that provides for a wide distribution or dispersion of cardioversion/defibrillation energy, using one or more small diameter elongated electrodes.

Some embodiments of the invention accomplish the distribution of cardioversion/defibrillation energy by means of a cardioversion/defibrillation and pace/sense lead for intra-cardiac implantation provided with a cardioversion/defibrillation electrode structure of multiple, small diameter exposed wire filaments which may be dispersed in a desired portion of a chamber of the heart or elsewhere, e.g., deep in the apex of the right ventricle for optimizing the ventricular cardioversion/defibrillation energy pathway. In some such disclosed embodiments, a pace/sense electrode may be affixed into contact with heart tissue, e.g. the myocardium, remote from the defibrillation electrodes. Some such embodiments of the invention also have one or more additional features, including a system and method for restraining the fine exposed wire filaments during transvenous introduction into a chamber or vessel for deployment therein, forming and shaping the fine exposed wire filaments to effect a wide dispersion on release from the restraint, and cardioversion/defibrillation electrodes which may be readily retracted after chronic use.

In a first embodiment, the distal ends of the wire filaments which make up the defibrillation electrode are free to enter the interstices of the trabeculae in the heart chamber. Segments of the wire filaments are formed with curvatures to effect the dispersion of the filaments apart and into the interstices. In a second embodiment, the ends of the wire filaments are attached by a weak bond to the lead extension adjacent to the pace/sense electrode. The weak bond at that junction may be pulled apart to ease chronic removal of the wire filaments by traction force applied proximally to the wire filaments. Preferably, the cardioversion/defibrillation conductor means for electrically connecting the cardioversion/defibrillation electrode to the proximal end of the lead body comprises extensions of the wire filaments extending proximally through lumens in the lead body. The extensions of the wire filaments may be accessed near the proximal end of the lead body and traction applied to effect chronic withdrawal of the wire filaments. In the second embodiment, the traction effects breaking of the weak bond followed by withdrawal of the wire filaments.

The first and second embodiments of the lead are preferably introduced with an introducer system for transvenously introducing the pace/sense electrode to the selected site and for allowing dispersion of the wire filaments of the cardioversion/defibrillation electrode adjacent to the selected site, the introducer means having: first means extending to the distal end of the lead body for guiding the pace/sense electrode to the selected site and for allowing the fixation means to effect attachment of the pace/sense electrode into contact with the heart at the selected site through manipulation of the proximal end of the lead body; and second means for restraining the plurality of elongated, un-insulated wire filaments from spreading apart from the lead body during introduction of the pace/sense electrode to the selected site.

In a preferred embodiment, the lead is inserted into the lumen of an elongated introducer sheath having a proximal end opening and a distal end opening with the pace/sense electrode and the plurality of elongated wire filaments extending distally from the distal end of the lead body and restrained closely together within the lumen and facing the distal end opening. The introducer sheath is preferably provided with means to deflect the distal end thereof to effect a desired placement of the pace/sense electrode.

The steps of introducing the lead preferably further comprise: advancing the introducer sheath with the lead inserted within the sheath lumen to a selected pace/sense site within the patient's heart chamber; advancing the pace/sense electrode from the distal end opening of the introducer sheath; fixing the pace/sense electrode into contact with the patient's heart at the selected pace/sense site; releasing the plurality of elongated wire filaments extending from the distal end of the lead body with respect to the distal end opening to disperse the elongated wire filaments apart; and withdrawing the introducer sheath proximally over the lead body. The release of the plurality of elongated wire filaments may be effected by withdrawal of the introducer sheath proximally over the lead body, whereby the wire filaments spread outward and away from the sheath end opening. Withdrawal of the sheath may include splitting the introducer sheath body to remove it from a lead body having a conventional enlarged proximal connector or by withdrawing the introducer over an isodiametric connector.

Advantageously, in a ventricular application of the lead of the first embodiment, the free ends of the individual electrode wire filaments are dispersed apart by deflection into interstices of the trabeculae of the right ventricle and electrically isolated thereby from the pace/sense electrode. The electrical isolation is enhanced by implantation of the pace/sense electrode into contact with the heart tissue at a point remote from the intended area of deployment of the wire filaments, prior to deployment of the wire filaments. The lead of the second embodiment may be implanted in the same manner, although the wire filament distal ends are prevented from being separately directed into trabecular interstices by the weak bond junctions.

As an alternative to accomplishing dispersion of the cardioversion/defibrillation energy by dispersing the small diameter defibrillation electrodes within the heart chamber, the inventors have also surprisingly learned that it is possible to rely on the conductivity of the blood within the heart chamber to accomplish dispersion of the cardioversion/defibrillation energy from a single, small diameter defibrillation electrode. In these embodiments, the lead body takes the form of a single, non-diverging filament, with the electrode located along or extending distally from the lead body, along the axis of the lead body. In these alternative embodiments of the invention, an electrode corresponding to a single one of the wire filaments employed in the first and second embodiments discussed above may be employed as the sole defibrillation electrode within a chamber of the heart.

In a third embodiment of the invention, the wire filament may be the only electrode on the lead, requiring the use of an additional lead carrying one or more pace/sense electrodes if they are desired for use in the chamber in which the defibrillation electrode is implanted. In a fourth embodiment of the invention, a slightly larger diameter defibrillation electrode is provided, which, while still substantially reduced in diameter as compared to comparable prior leads, has sufficient cross sectional area to allow inclusion of a second conductor so that a pace/sense electrode may be included on the lead.

In conjunction with leads according to the third and fourth embodiments of the invention, the lead may optionally be provided with a sliding, insulative sheath, allowing adjustment of the exposed length of the defibrillation electrode. The configuration of both the third and fourth embodiments of the present invention may be optimized to produce a small over-all diameter by fabricating the exposed defibrillation electrode as part of the same wire or cable which couples the defibrillation electrode to an implantable cardioverter/ defibrillator, avoiding the increase in lead diameter often necessitated by mechanical interconnection of electrodes and conductors.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIGS. 1–3 are perspective views of the distal end of a first embodiment of the cardioversion/defibrillation lead of the present invention positioned in relation to an introducer sheath during stages of implantation or removal thereof;

FIG. 16 is a perspective views of the distal end of a variation on the second embodiment of the cardioversion/ defibrillation lead of the present invention positioned in relation to an introducer sheath during stages of implantation or removal thereof; and FIG. 17 is a cross-section view taken along lines B—B of a conductive connector in the distal end of the lead of FIG. 16.

The drawings are not necessarily to scale.

Figure 18:
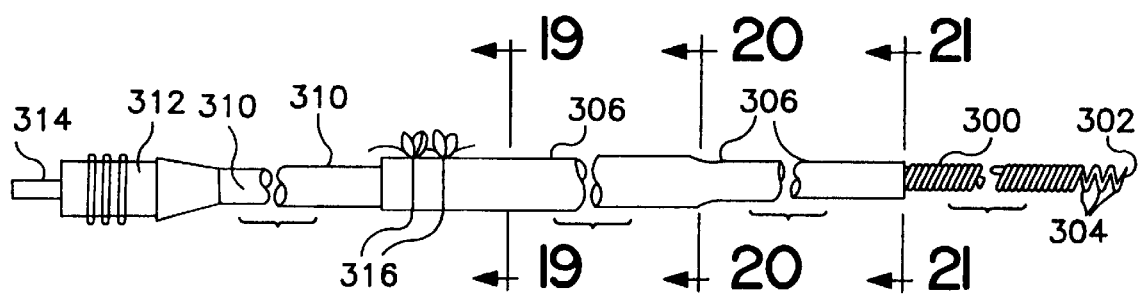

FIG. 18 is a plan view of a third alternative embodiment of a lead according to the present invention.

Figure 19:
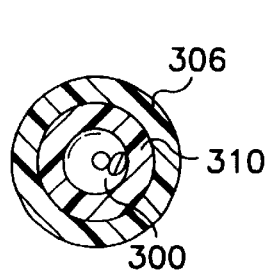
Figure 20:
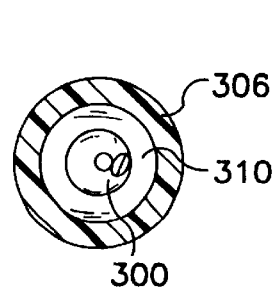
Figure 21:
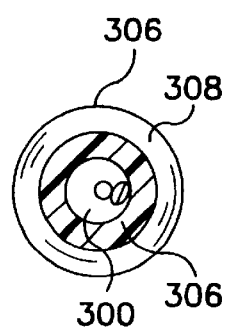

FIGS. 19, 20, and 21 are cross-sections through the lead illustrated in FIG. 18.

Figure 22:
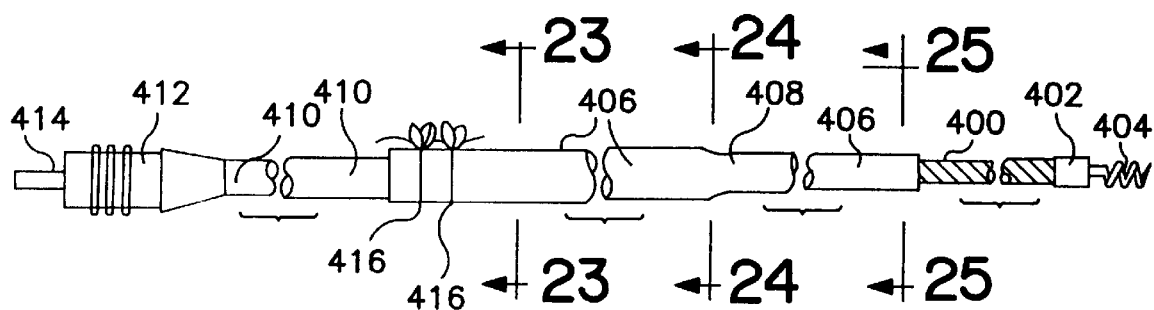

FIG. 22 is a plan view of a variant of the lead illustrated in FIG. 18.

Figure 23:
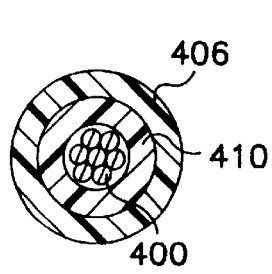
Figure 24:
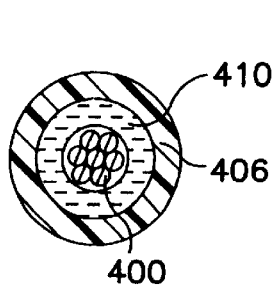
Figure 25:
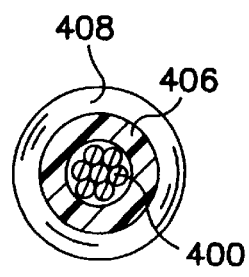

FIGS. 23, 24 and 25 are cross-sections through the lead illustrated in 22.

Figure 26:
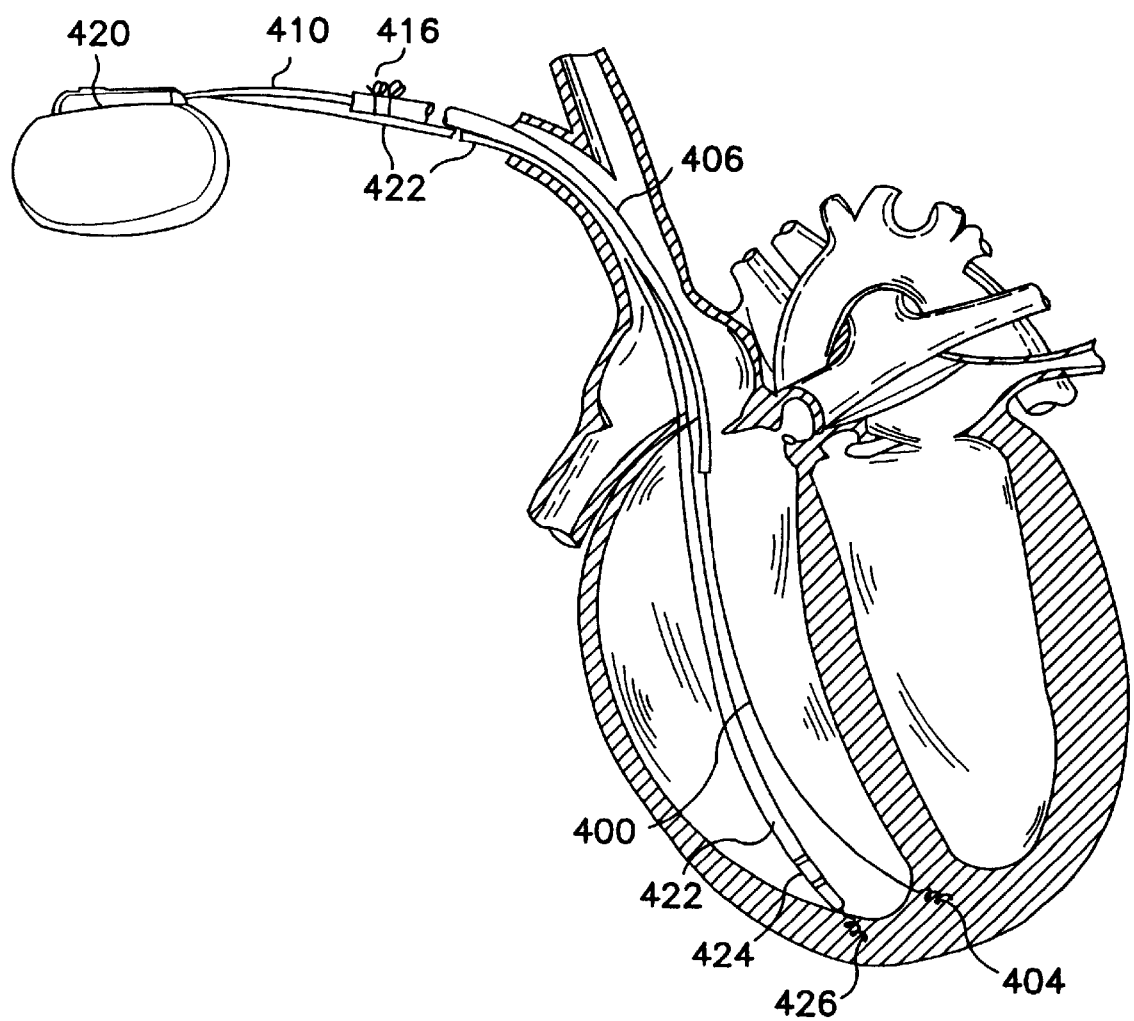

FIG. 26 illustrates the method of use of the leads illustrated in FIGS. 18 and 22.

Figure 27:
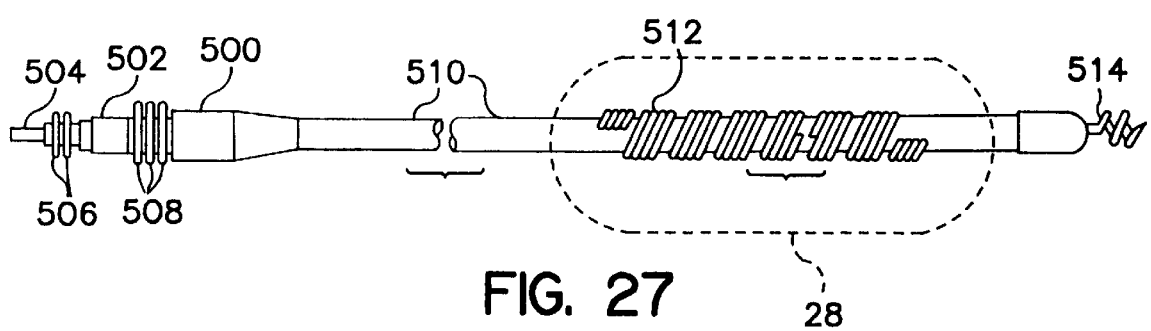

FIG. 27 illustrates a fourth alternative embodiment of the lead according to the present invention.

Figure 28:
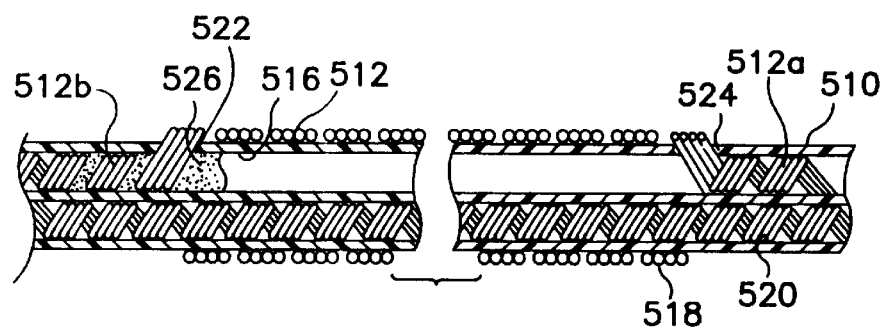

FIG. 28 is a side, cutaway view of a portion of the distal end of the lead illustrated in FIG. 27.

Figure 29:
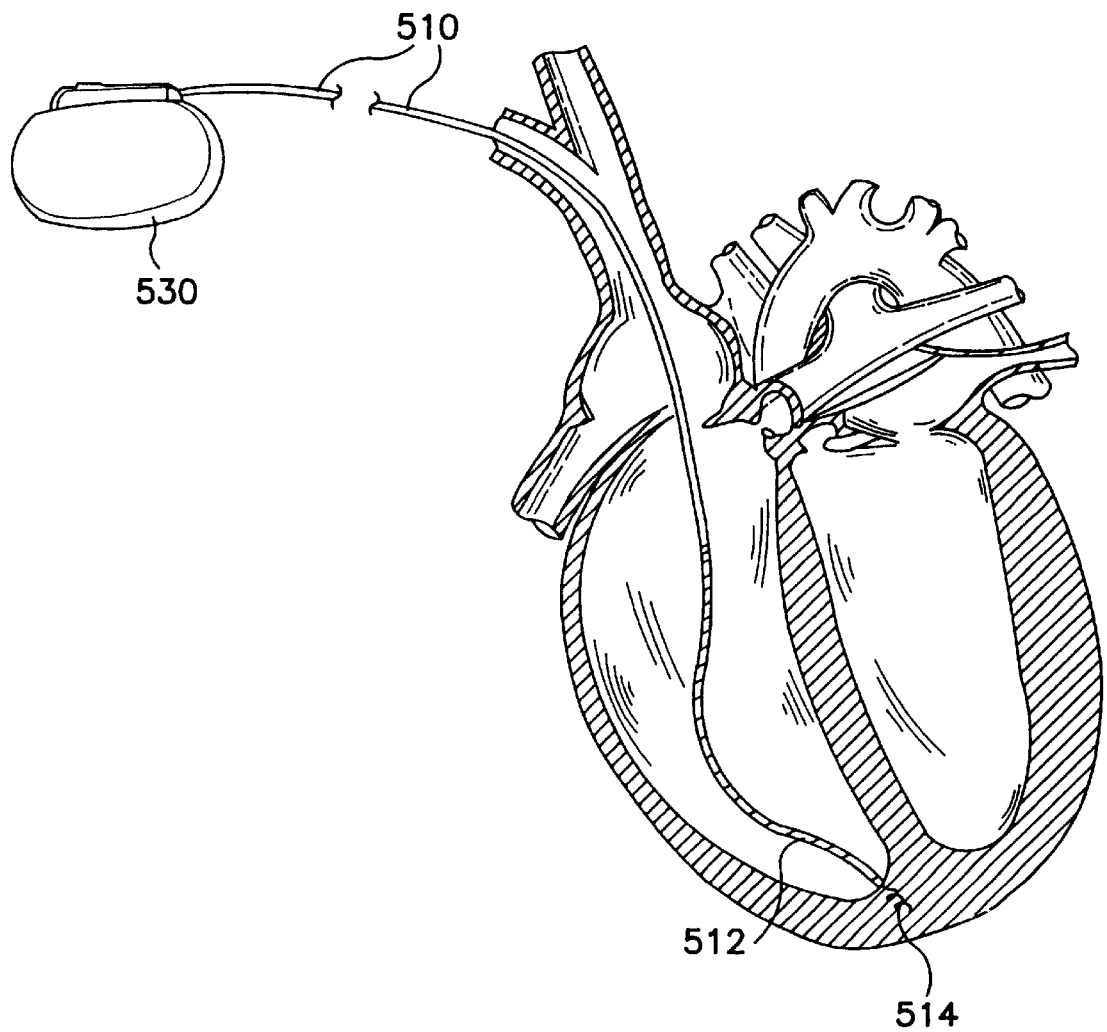

FIG. 29 illustrates a method of use of the lead illustrated in FIG. 27.

Figure 1:
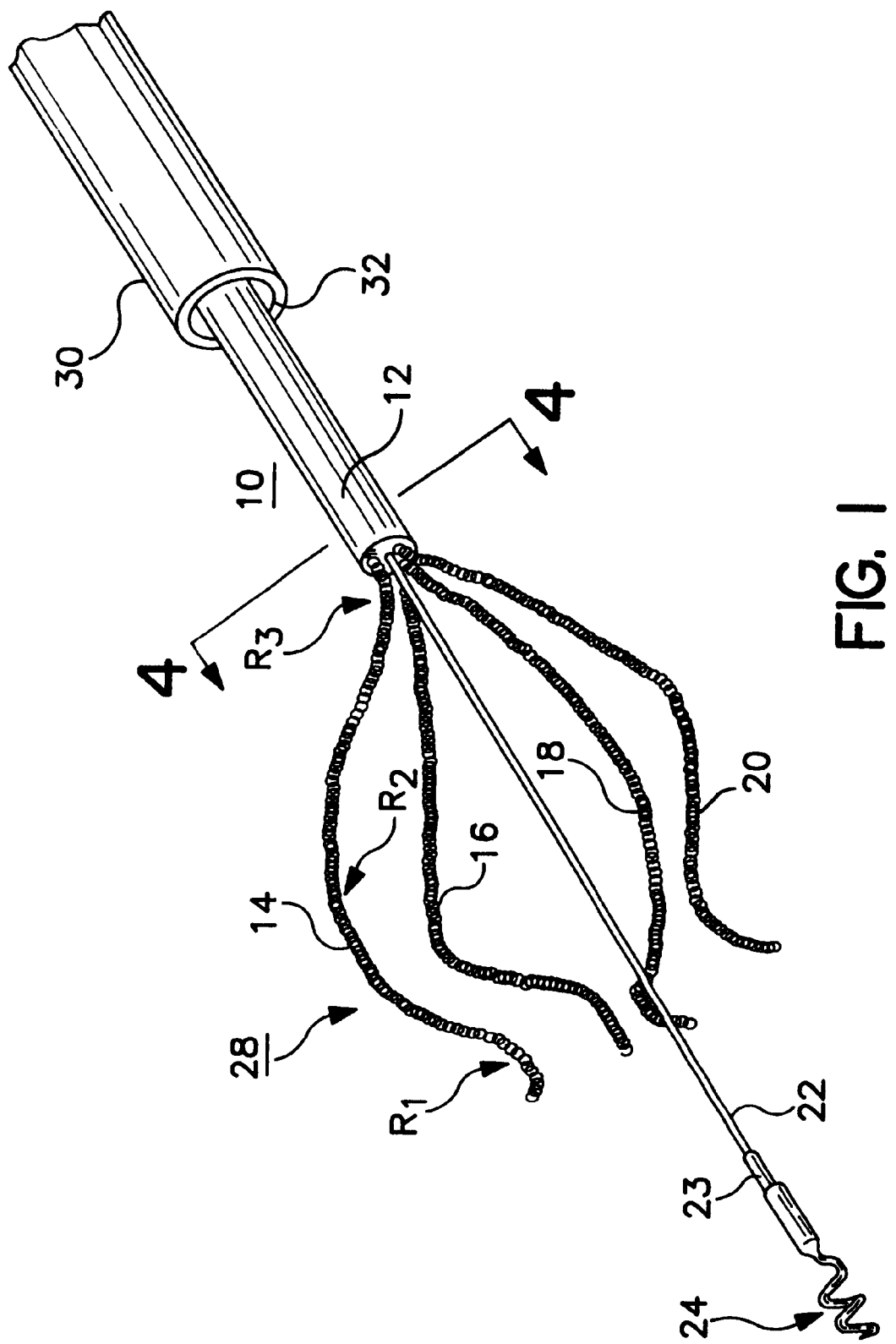
Figure 30:
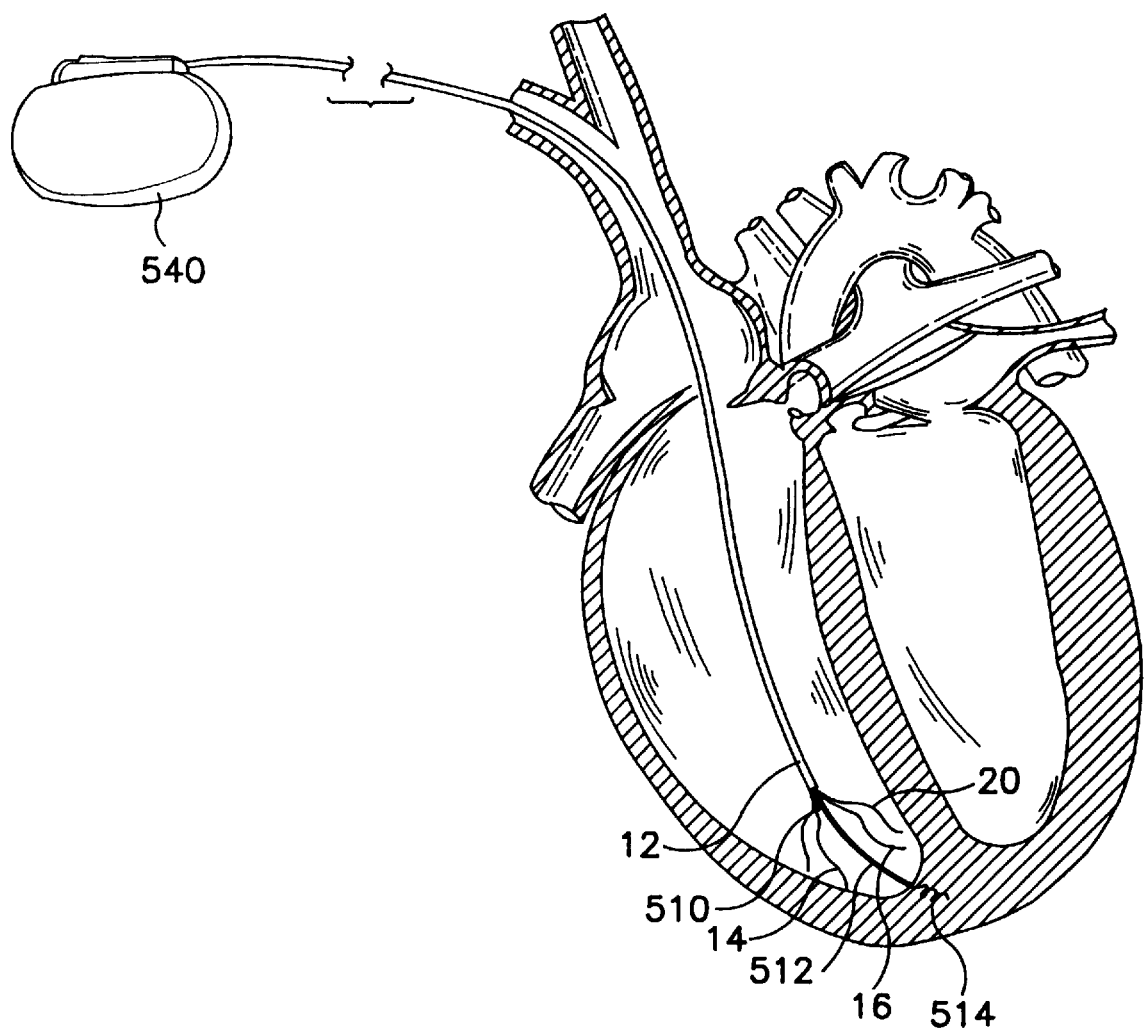

FIG. 30 illustrates an alternative use of the lead illustrated in FIG. 27, incorporated as part of a lead otherwise as illustrated in FIG. 1.

DETAILED DESCRIPTION OF THE PREFERRED EMBODIMENTS

Figure 9:
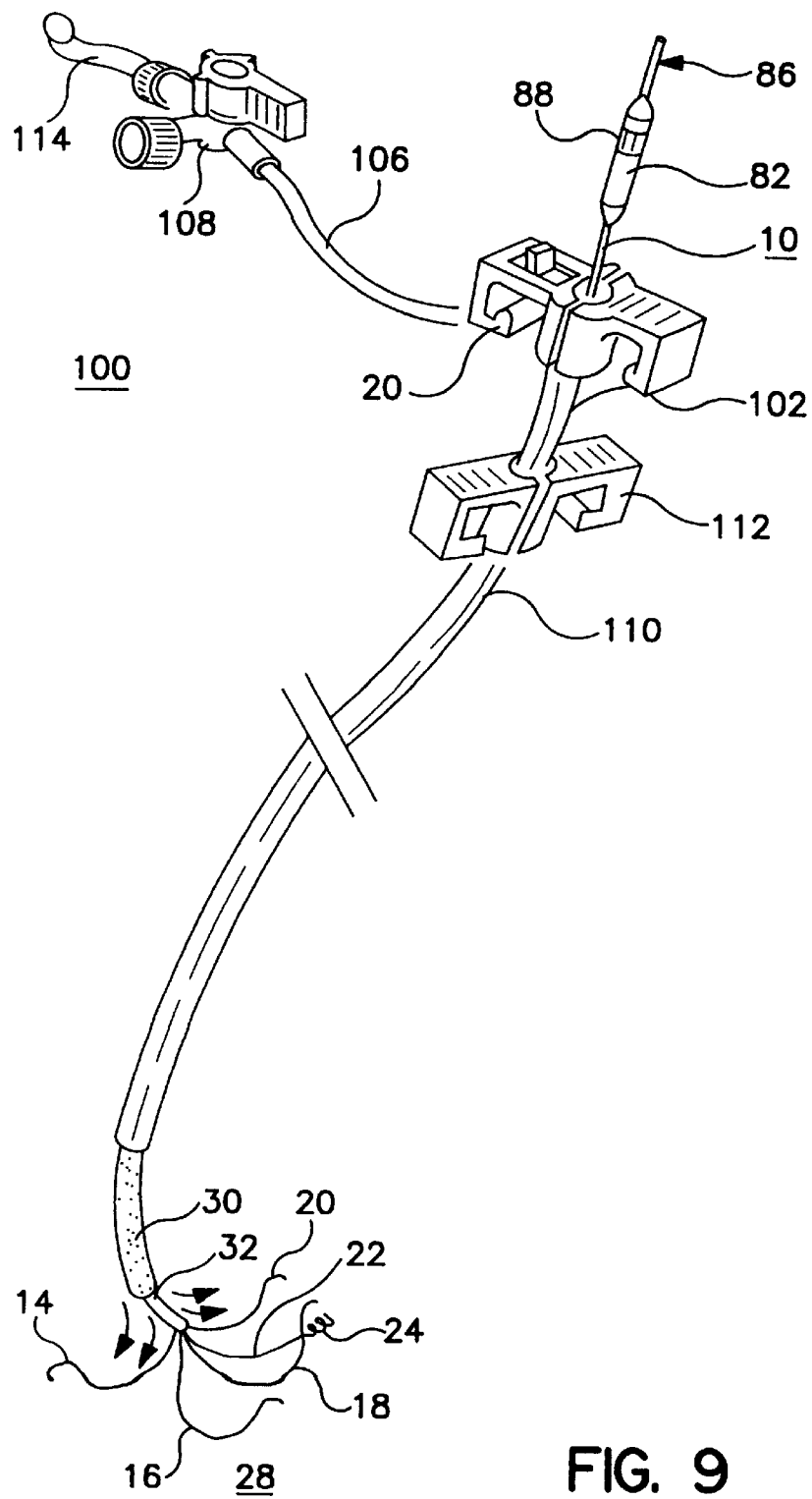
FIGS. 9 and 10 are perspective views of one preferred embodiment of an introducer system for introducing the cardioversion/defibrillation lead of the present invention and deploying the pace/sense and cardioversion/defibrillation electrodes.
Figure 10:
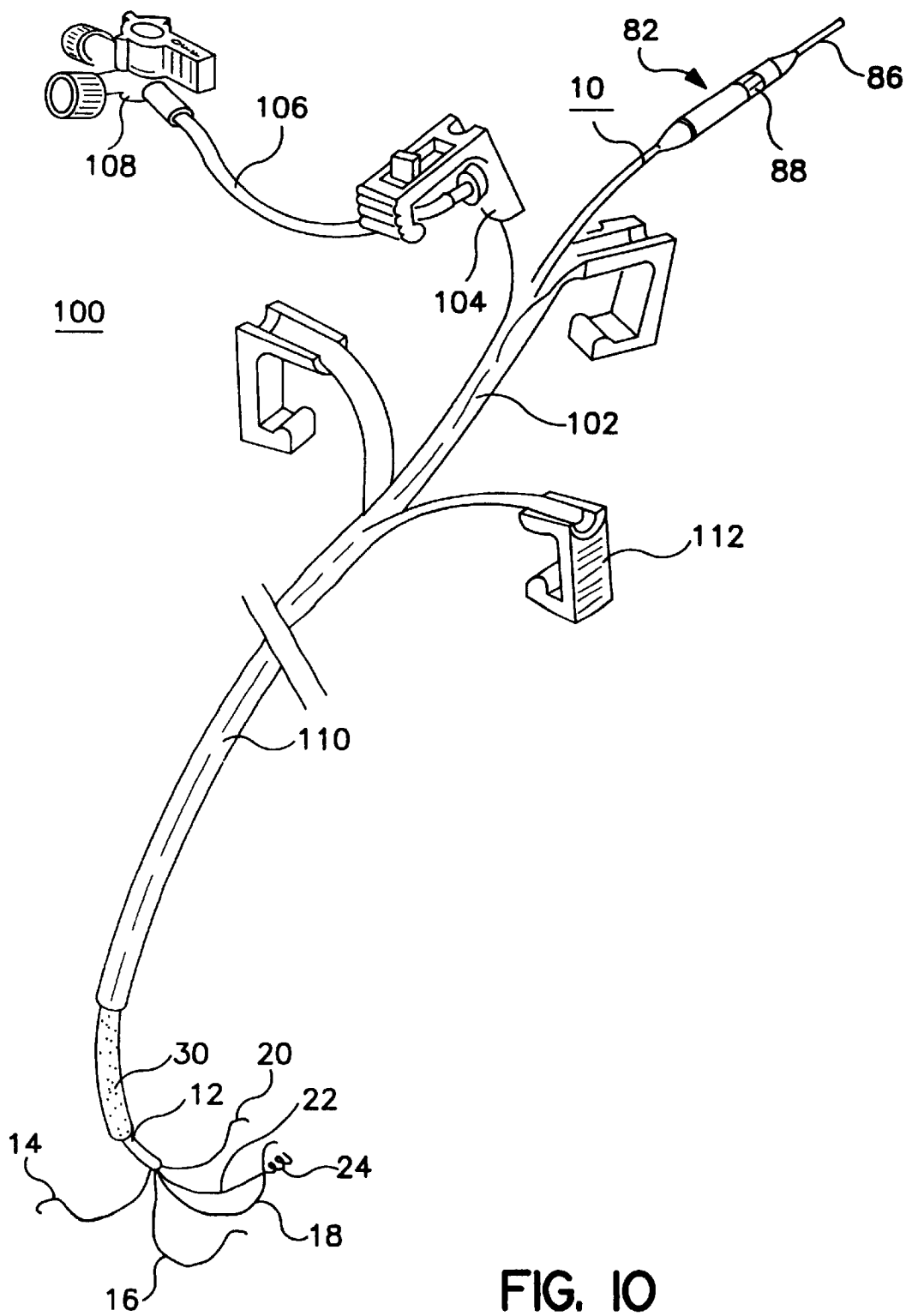

The present invention is realized in a number of preferred embodiments and variations thereof as described in detail hereafter. It will be understood that specific features of the invention that may be implemented in any of the embodiments and variations thereof are depicted in one or more of the figures and/or described herein. FIGS. 1–3 and 7–8, and the variation of FIGS. 16 and 17, illustrate first and second embodiments of the invention employing either fine coiled or stranded conductor wires depicted in FIGS. 4–6 as wire filaments of the cardioversion/defibrillation electrode. One embodiment of an introduction catheter assembly for effecting the introduction of the cardioversion/defibrillation lead is depicted in FIGS. 9 and 10. Implant locations of the pace/sense electrode and the cardioversion/defibrillation electrode wire filaments are depicted in FIGS. 11–15.

Turning to FIG. 1, it is a perspective view of the distal end segment of a first embodiment of the cardioversion/ defibrillation lead 10 of the present invention completely advanced out of the distal end opening 32 of an introducer sheath 30 (preferably an inner introducer sheath as described below). The lead 10 comprises an elongated lead body 12 of an electrically insulating material, e.g. medical grade silicone rubber or thermoplastic polymer, having a proximal end connector attached thereto and a distal end from which a plurality, e.g. four, elongated, un-insulated wire filaments 14, 16, 18, and 20 from a point of attachment thereto and a centrally disposed pace/sense lead extension 22 extend distally from the point of attachment thereto. The distal ends of the wire filaments 14, 16, 18, 20 and the distal end of pace/sense lead extension 22 may also be viewed as comprising the distal end of the lead body.

The lead extension 22 includes an electrical conductor that is electrically insulated through its length and terminates in a distal, pace/sense, helical screw-in electrode 24 that is adapted to be rotated and screwed into the myocardium during the introduction and fixation process. The lead extension 22 and helical electrode 24 may take the form of the miniaturized helical screw-in leads of commonly assigned U.S. Pat. No. 5,246,014, incorporated herein by reference in its entirety. As disclosed therein, the helical distal electrode 24 is formed of fine platinum-iridium alloy wire having a diameter of about 0.006 inches that is drawn into a helix of a diameter between 0.027 and 0.058 inches. The helical distal electrode 24 provides attachment and contact with the heart at a selected site within the selected heart chamber. The electrode 24 may be screwed into the myocardium through manipulation of the proximal end of the lead body and/or the proximal end of an introducer engaging a distal lead crank portion as disclosed in the U.S. Pat. No. 5,246,014.

The conductor within the insulating sheath of lead extension 22 may be formed of an electrically insulated multi-strand cable or helical coil of materials typically used in pace/sense lead conductors including MP35N alloy having an overall diameter of 0.003 to 0.020 inches. Due to the small diameter, a more radiopaque metal, e.g. platinum-iridium alloy helical coil or a silver core wire multi-strand cable, may be preferred to enhance visibility under fluoroscopy. The conductor of the pace/sense lead extension 22 is preferably encased within a sheath of silicone rubber or a dielectric fluoropolymer material, e.g. PTFE, ETFE or THV200. In the latter case, the sheath preferably has a wall thickness on the order of 0.006 inches. The preferred total outer diameter of lead extension 22 is on the order of about 0.027 inches or 2 French for the unipolar pace/sense lead shown.

In a bipolar pace/sense/electrode version, a ring electrode would be formed in lead extension 22 proximal to helical screw-in electrode 24 and a separate conductor would be encased within lead extension 22 in a manner well known in the pacing art The total outer diameter would then be on the order of about 0.039 inches or 3 French.

The fine, elongated wire filaments 14, 16, 18, and 20 are electrically connected in common within the lead body 12 and form the distributed cardioversion/defibrillation electrode 28 when deployed into the interstices of the trabeculae from midway down the right ventricular cavity and into the apex thereof The wire filaments 14, 16, 18, 20 are preferably formed of either fine wire strands twisted into cables as described in the above-incorporated U.S. Pat. No. 5,246,014 or in the above-referenced '332 application, incorporated herein by reference or preferably of fine a single-filar or multi-filar wire coils of the type described in commonly assigned U.S. Pat. No. 5,303,704, incorporated by reference in its entirety. The cables of fine wire strands or the coils are preferably formed of a low resistance, high current capacity metal, e.g. platinum-iridium alloy or a composite, e.g. a silver core wire that may be coated with platinum.

When the filaments 14, 16, 18, 20 are formed in wire coils of close wound coiled wire, the coiled wire diameter is preferably on the order of 0.004 inches, and the coil diameter is preferably about 0.015 inches. With the close winding and the small resulting coil lumen, it is unlikely that tissue ingrowth will occur into the coil lumen and between the coil turns, and it is preferred that the wire coil lumens in this size range be left open. To minimize any possibility of tissue ingrowth, particularly with larger coil lumens and/or space wound coil turns, the coil lumens may be filled with an elastic, body compatible silicone rubber or polyurethane compound.

When the filaments 14, 16, 18, 20 are formed of wire strands, the wire strands are preferably formed of 3–7 strands of fine wire having a diameter of 0.001 inches, for example, wound into cables as described in the U.S. Pat. No. 5,246,014. A number of the cables may themselves be twisted together to form enlarged cables. For example, enlarged cables may be formed of seven cables each formed of seven strands to form a forty-nine strand enlarged cable. Each seven strand cable has a diameter of about 0.0036 inches, and the enlarged cable has a diameter of about 0.0108 inches. In addition, either the seven strand cable or the forty-nine strand cable may itself be wound into a loose coil of a somewhat larger diameter.

In one preferred embodiment, the wire filaments 14, 16, 18, 20 are attached at their proximal ends to the distal end of a cardioversion/defibrillation lead conductor 42 encased within the lead body 12 in the region of the section A—A view of FIG. 1. The attachment may also be at the proximal end of the lead body at or adjacent to the connector 80. In the first attachment variation illustrated in FIG. 4, the cardioversion/defibrillation lead conductor 42 extends from a connector ring at the proximal end of the lead body 12 to the distal end proximal to section A—A of FIG. 1 and is a multi-filar coil wire that is wound about inner silicone tube 44 within the lumen 46 of outer tube 48. The outer silicone rubber tube 48 preferably has an outer diameter on the order of 0.053–0.066 inches or 4–5 French.

The lumen 50 of inner tube 44 receives the pace/sense conductor 52 that extends distally in pace/sense lead extension 22. The inner tube 44 may constitute the outer insulating tube of the pace/sense lead extension 22. The pace/sense conductor 52 may also constitute the wire strand cables described above. In this case, the multi-filar wire strands of the cable may be solidly encased in insulation forming the inner tube 44.

Figure 4:
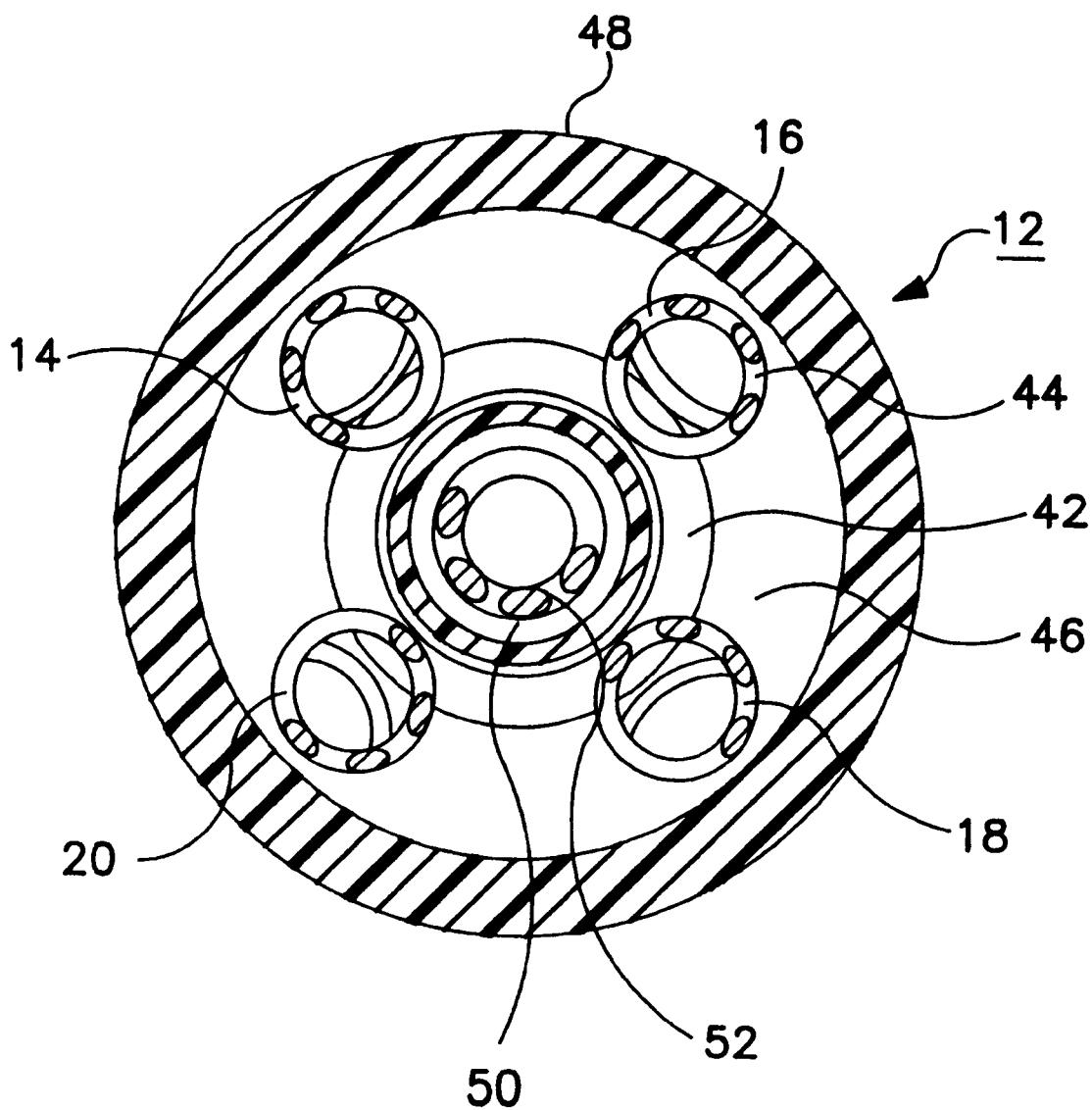
FIG. 4 is a cross-section view of the components of the lead body taken along lines A—A of FIG. 1.

The attachment of the wire filaments 14, 16, 18, 20 at their proximal ends to the distal end of a cardioversion/ defibrillation conductor 42 may be effected by welding or crimping in a manner well know in the art. Although the wire filaments 14, 16, 18, 20 are depicted in FIG. 4 as wire coils, it will be understood that they may be formed from the above-described, multi-filer wire strand cables or enlarged cables in straight or loose coil configuration and attached to the distal end of the cardioversion/defibrillation conductor 42 in manner described in the above-referenced '332 application.

Although a single point of all of the proximal ends of the wire filaments 14, 16, 18, 20 at the distal end of the lead body is depicted, it will be understood that separate attachments may be made at separate points along the lead body for each or for groups of the wire filaments.

Figure 5:
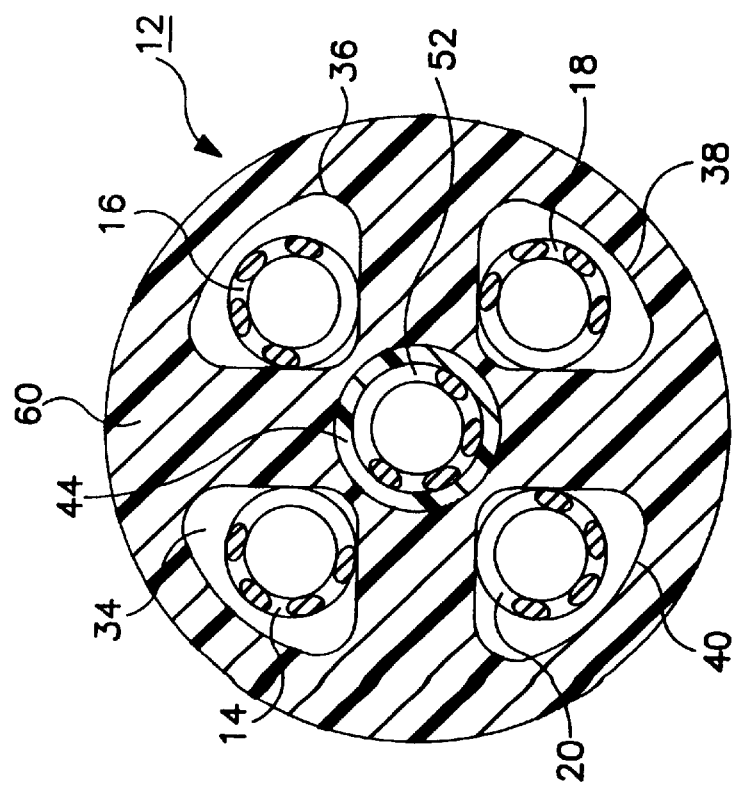
FIG. 5 is a cross-section view of a first variation of the components of the lead body taken along lines A—A of FIG. 1.

The removal of the cardioversion/defibrillation wire filaments 14, 16, 18, 20 from the right ventricle after chronic use may be a cause for concern due to fibrosis that may extend around and between the filaments at the distal end of lead body 12. In FIG. 5, a first variation is depicted wherein the cardioversion/defibrillation conductor 42 is replaced by extensions of the cardioversion/defibrillation wire filaments 14, 16, 18, 20 to the proximal end of the lead body. In this variation, all of the cardioversion/defibrillation wire filaments 14, 16, 18, 20 are formed as wire coils that extend into pie shaped lumens 34, 36, 38, 40, respectively, formed in extruded lead sheath 60. The pace/sense conductor 52 is formed of a wire coil within the inner sheath 44 that extends to form the pace/sense lead extension 22.

The cardioversion/defibrillation wire filaments 14, 16, 18, 20 are formed as continuous wire coils that extend back through pie shaped lumens 34, 36, 38, 40, respectively to the proximal end of the lead 10. In this variation, the pie shaped lumens loosely receive the cardioversion/defibrillation wire filaments 14, 16, 18, 20 in the manner described in the above-referenced U.S. Pat. No. 5,303,704. The pie shaped lumens 34, 36, 38, 40 may be coated with a friction reducing agent, such as PTFE; or the like adhered thereto by a plasma treatment, to provide for easy insertion and removal of the cardioversion/defibrillation wire filaments 14, 16, 18, 20 therethrough. In the second variation of FIG. 6, the cardioversion/defibrillation wire filaments 14, 16, 18, 20 and the pace/sense conductor 52 are depicted as seven wire strand cables of the type described in the above-incorporated U.S. Pat. No. 5,246,014 or as an enlarged cable of seven cables of seven strands each of the type described in the above-incorporated '332 application. The pace/sense conductor 62 is encased within an inner sheath 64 that extends to form the pace/sense lead extension 22. The cardioversion/defibrillation wire filaments 14 16, 18, 20 are enclosed inside circular, coated lumens 54, 56, 58, 60 within the solid extruded lead body 12.

Figure 6:
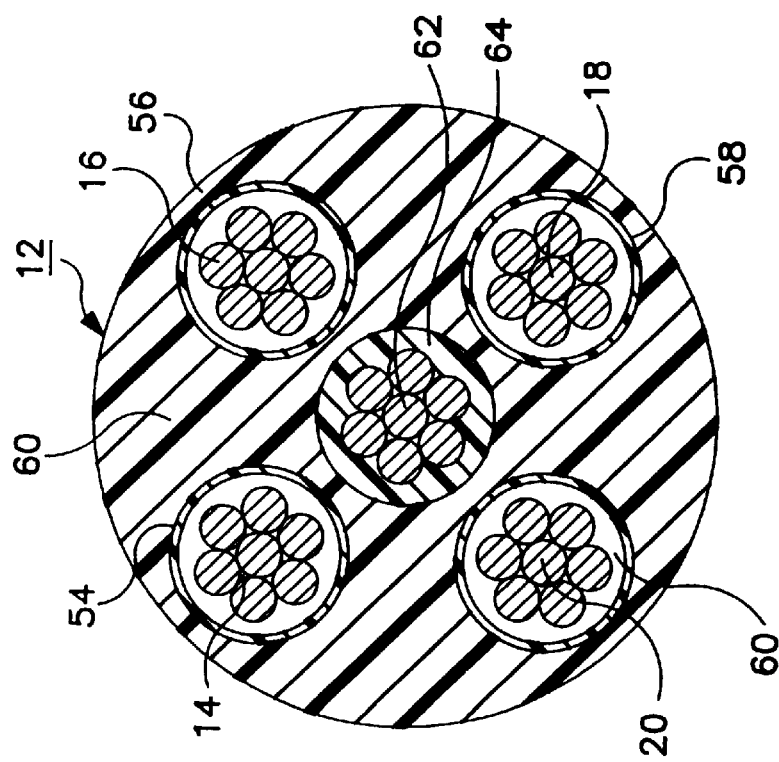
FIG. 6 is a cross-section view of a second variation of the components of the lead body taken along lines A—A of FIG. 1.

In these variations of FIGS. 5 and 6, removal after chronic implantation may be facilitated by the selective individual retraction of each of the cardioversion/defibrillation wire filaments 14, 16, 18, 20 at least into the lumens 34, 36, 38, 40 or 54, 56, 58, 60. At the proximal end of the lead 10, removal may be effected by stripping away the extruded lead sheath 60, clamping the exposed wire filaments and applying tension until the clamped wire retracts the filament back through or into its respective lumen. After all of the wire filaments are retracted, the proximal lead body and wires may be trimmed away and an introducer sheath may be advanced distally over the remaining lead body. When the introducer sheath is advanced to the proximal end of the helical pace/sense electrode 24, the entire lead body 12 and sheath may be rotated to un-screw the helical pace-sense electrode 24. Then, the entire lead 10 and introducer may be transvenously withdrawn.

Alternatively, it is contemplated that the small diameter, small gauge, and relatively ductile helical screw pace/sense electrode 24 may be straightened out and retracted by traction applied to the proximal end of the lead body without causing any clinically significant harm to the heart tissue. Given the small diameters of the filaments 14, 16, 18, 20, it may be possible that retraction of the entire lead body may be first tried before resorting, if necessary, to the retraction of the individual filaments as described above.

It should be noted that coiled wire conductors and electrode filaments constructed as described above in reference to FIGS. 4 and 5 may stretch considerably if the filaments are strongly embedded in chronic tissue ingrowth and are retracted from the proximal end as described above. In one further variation, the wire coil filaments and the wire strand cables described above may be combined together to prevent the stretching and provide increased surface area and improved conductivity. In this variation composite wire filaments 14, 16, 18, 20 may be formed of a solid platinum-iridium wire or coated platinum-iridium wire coil formed around the wire strand cable, and the wire strand cable may be attached thereto at the distal filament ends. Preferably, the wire coils terminate and are attached to the inner wire strand cables at the sections depicted in FIGS. 4–6. In effect, the electrical and mechanical performance of the wire strand cable embodiment may be enhanced by the surrounding wire coil, and significant stretching may be avoided during retraction.

Returning to the description of the first embodiment having distal wire filament free ends, FIG. 2 is a perspective view of the distal end retracted into the lumen of the introducer sheath 30 so that only the helical screw-in electrode 24 is exposed at the end opening 32 in a position to be screwed into or out of the myocardium. As described below, the helical pace/sense electrode 24 is first screwed into the myocardium at a selected site while the cardioversion/defibrillation wire filaments 14, 16, 18, 20 remain within the lumen of introducer sheath 30. This effectively immobilizes and electrically isolates the helical pace/sense electrode 24 before the cardioversion/defibrillation wire filaments 14, 16, 18, 20 are deployed.

FIG. 3 is a perspective view of the distal end of the cardioversion/defibrillation lead 10 advanced partly out of the end opening 32 of introducer sheath 30 after fixation of the distal helical pace/sense electrode 24 into the myocardium (not shown) to commence deployment of the cardioversion/defibrillation wire filaments 14, 16, 18, 20 into the interstices of the trabeculae of the heart. The wire filaments 14, 16, 18, 20 inherently have a spring bias and are shaped to have a curl in the tips thereof that is evident immediately as they begin to be deployed as shown in FIG. 3. The curl and any other more distal curvature causes the tips to spread apart like fingers of a hand opening up from a fist and to extend distally generally in parallel. Within the right ventricle, this causes the tips to enter interstices of the trabeculae at spaced apart locations. To effect this initial routing of the electrode tips, the particular unrestrained overall shape of the wire filaments 14, 16, 18, 20 is not as important as the slight curl at the tips thereof having a distal minor radius $R_1$ shown in FIG. 1.

With further advancement of the lead 10 and retraction of the introducer 30, the wire filaments 14, 16, 18, 20 are advanced into the interstices of the trabeculae and are separated from one another by the trabecular structure that is encountered. In clinical implantation in the right ventricle, some of the filaments may be blocked and forced aside and others may extend forward, depending on the trabecular structure encountered. The overall spreading may be on the order of inches apart in all directions, causing a wide distribution or dispersion of the cardioversion/defibrillation electrode 28.

It should be understood that the relative lengths and degrees of curl of the wire filaments 14, 16, 18, 20 may be varied so that the spreading apart is not necessarily uniform. The filament lengths may also be longer or shorter, or some of both, than the length of the lead extension 22. The trabeculae encountered in the heart chamber may also inhibit the degree of spreading and otherwise ensure that the spreading apart of the wire filaments will not be uniform.

Referring back to FIG. 1, for example, filament 14, having an overall free length of 2.5 inches, for example, may have three radii of curvature in three segments thereof indicated by the distal minor radius $R_1$, the intermediate major radius $R_2$, and the proximal minor radius $R_3$. These radii of curvature are preferably, but not necessarily, in the same plane. The minor radius $R_1$ is preferably 15/64 inches, the intermediate radius $R_2$ is preferably between 15/32–24/32 inches, and the proximal minor radius $R_3$ is preferably between 9/128 and 10/128 inches, with a tolerance on the order of 20%. In combination, four (or fewer) filaments of the same 2.5 inch length may have the following radii, for example:

|    | $R_1$   | $R_2$   | $R_3$    |
|----|---------|---------|----------|
| 14 | 15/64   | 15/32   | 9/128    |
| 16 | 15/64   | 3/4     | 5/64     |
| 18 | 15/64   | 5/8     | 5/64     |
| 20 | 15/64   | 5/8     | 9/128    |

Although no indication exists that there is any necessity of doing so, it may prove desirable to stiffen the distal free ends of the filaments 14, 16, 18, 20 to strengthen the distal minor radii $R_1$ and provide a greater degree of control as they are advanced out of the end opening of the catheter introducer lumen. The intermediate and proximal segments should be left with the inherent flexibility of the above-described materials, shapes and sizes to provide an overall filament flexibility that avoids any possibility of end loading the filament and perforating the heart wall. In the open wire coil and wire strand cable filament embodiments, including the composite wire coil and wire strand cable variation, the stiffening may be effected by providing a stiffening wire in the lumen of the distal segment. In the open coil or the filled coil variation, a high durometer silicone or polyurethane plug material may be used in the distal segment lumens of the coils of the wire coil filaments to effect a stiffening thereof. Alternatively, in the stranded wire cable embodiment and the composite wire coil and wire strand cable filament variation, a shrink tube can be placed over a distal end portion at or just proximal to the tip to provide some degree of localized stiffness.

Figure 7:
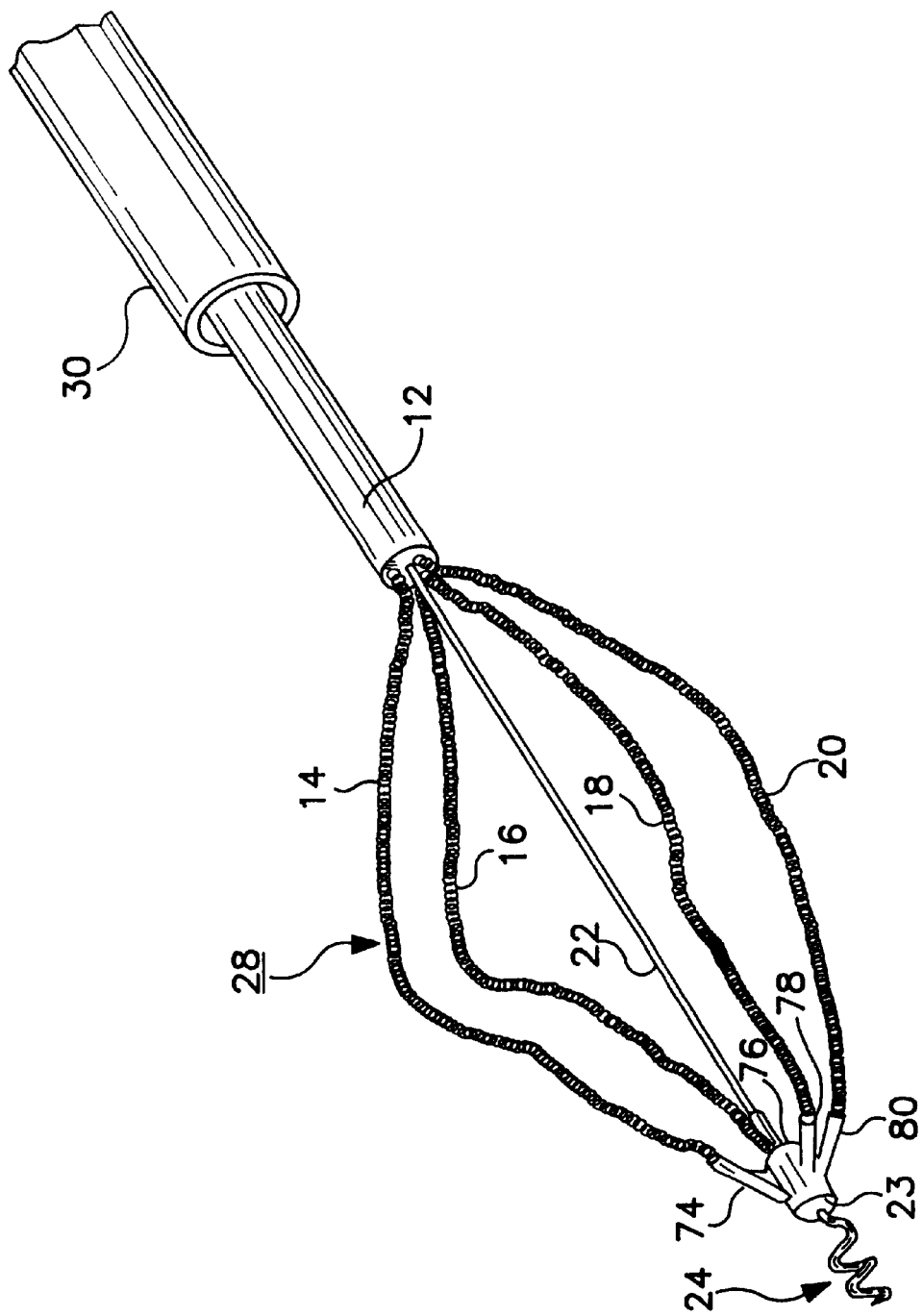
FIGS. 7 and 8 are perspective views of the distal end of a second embodiment of the cardioversion/defibrillation lead of the present invention positioned in relation to an introducer sheath during stages of implantation or removal thereof.
Figure 8:
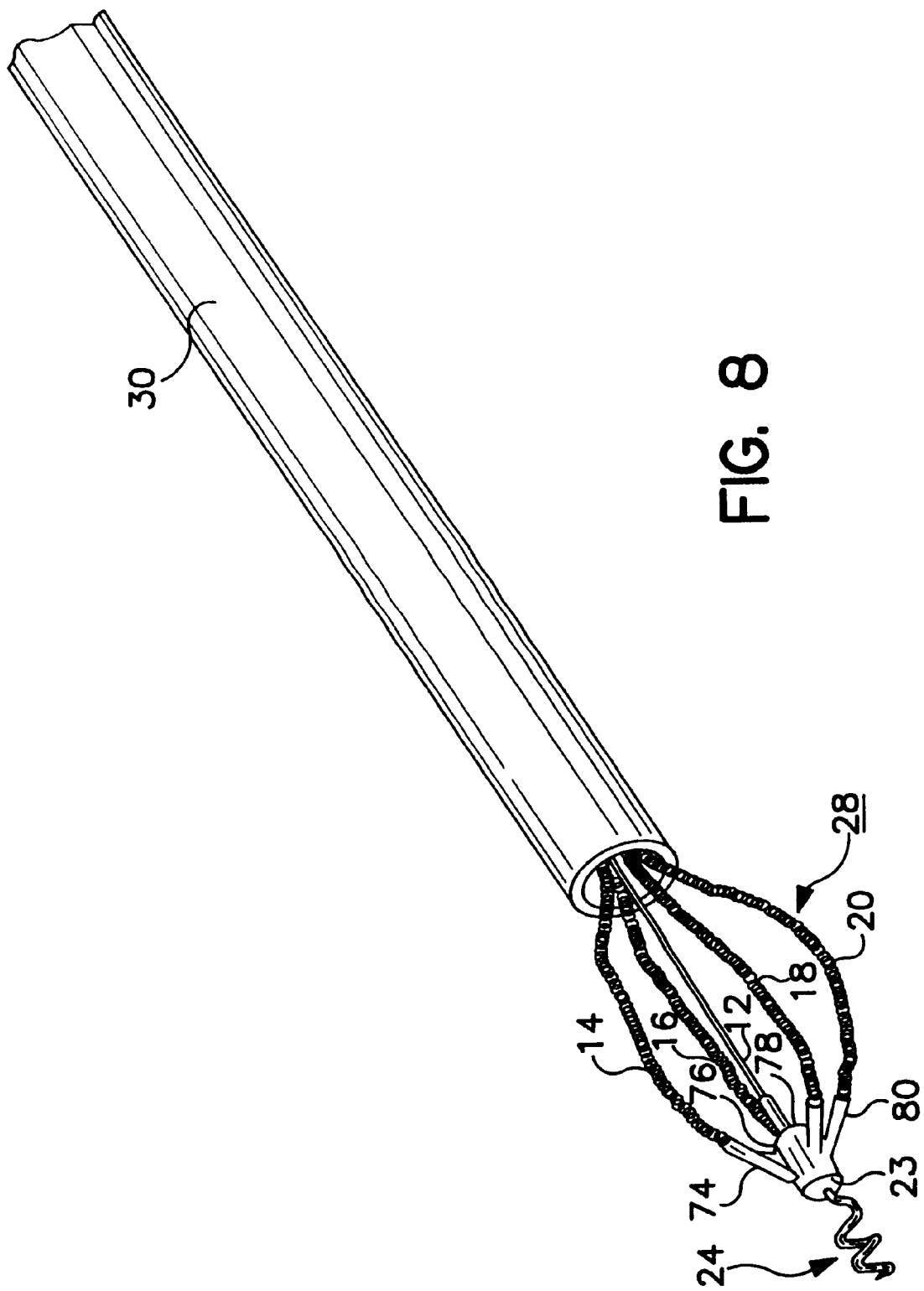

Turning to FIGS. 7 and 8, a further embodiment of the lead 10 of the present invention is depicted which is configured and operates in a somewhat different fashion than the embodiment and variations described above. A number of the above-described prior art patents have proposed bifurcated cardioversion/defibrillation lead body and electrode configurations that would be difficult if not impossible to remove after fibrosing in. The first embodiment described above obviates that concern because the ends of the wire filaments 14, 16, 18, 20, are free and can be removed from the interstices and the fibrosis around the wire filaments by traction.

However, there could be some concern that one or more of the wire filaments 14, 16, 18, 20, might contact the helical electrode 24 if it is not placed properly. In the embodiment illustrated in FIGS. 7 and 8, the straightened tips of the wire filaments 14, 16, 18, 20 are restrained by penetration into polymer projections 74, 76, 78, 80 (preferably formed of silicone rubber) that extend outwardly a short distance from the slightly enlarged insulated attachment junction 23 of the pace/sense helical electrode 24 and the lead extension 22 to form a relatively weak bond therebetween. The weak bond may also be effected by making the projections 74, 76, 78, 80 with narrowed cross-sections at the bases of projection from the insulated attachment junction 23. The projections 74, 76, 78, 80 depicted in FIGS. 7 and 8 are somewhat exaggerated in overall size for ease of illustration.

FIGS. 7 and 8 show the partial and full deployment of the wire filaments 14, 16, 18, 20 from the introducer sheath 30 while remaining attached distally by the weak bond to the projections. During chronic implantation, fibrotic tissue will grow around the polymer projections 74, 76, 78, 80. However, when traction is applied to the wire filaments 14, 16, 18, 20, the straightened ends thereof can easily be pulled out of the projections 74, 76, 78, 80 breaking the bond therebetween. The free ends may then be retracted through the fibrotic tissue in the manner described above. The various constructions of the wire filaments 14, 16, 18, 20 described above in respect to FIGS. 4–6 may be employed in this embodiment.

Turning to FIGS. 16 and 17, a further variation on the second embodiment is depicted, wherein the distal ends of the filaments 14, 16, 18, 20 are engaged in a releasable fashion in a conductive connector 90 whereby the tips are electrically connected together and can still be pulled away from the insulated attachment junction 23. The weak bond is effected by an elongated conductive ring 92 slipped over the outer insulation at or near the insulated junction 23 and an insulating shrink band 94 that traps the filament ends therebetween. The conductive ring 92 may be formed with elongated cylindrical grooves $96_{14}$, $96_{16}$, $96_{18}$, $96_{20}$, for receiving each of the filament ends before the shrink band 94 is shrunk over them. This arrangement forms a weak bond so that the filament ends may be released by traction along the lengths of the filaments 14, 16, 18, 20 as described above. The common electrical connection afforded by conductive ring 92 may contribute to the overall effective impedance of the cardioversion/defibrillation electrode 28. Other equivalent structures may be substituted for conductive connector 90, e.g. 90° pie shaped segmented conductive blocks formed around the filament ends and held together around the insulated junction 23 by the band 94 or other pin and socket arrangements employed in electrical connectors.

It should be noted that the wire filaments 14, 16, 18, 20 when straightened to fit within the introducer sheath lumen are preferably of equal length and also of the same length as the pace/sense lead extension 22 in order to minimize the required size of the introducer sheath lumen. It should also be noted that the lead extension 22, like the wire filaments 14, 16, 18, 20 need be straight when unrestrained by the introducer sheath lumen as shown in FIG. 16. The wire filaments 14, 16, 18, 20 may be made longer than the length as the pace/sense lead extension 22, but would have to be wrapped around the pace/sense lead extension 22 to be inserted into an introducer sheath lumen of somewhat larger size.

In all of the above-described embodiments and variations of the lead 10, it may be desirable to electrically insulate a portion or portions of the filaments 14, 16, 18, 20 so that the effective cardioversion/defibrillation electrode surface area and location may be modified to enhance current distribution for the particular intended placement of the lead. For example, in order to attain a greater separation of the cardioversion/defibrillation electrode 28 from the distal pace/sense electrode(s) 24 in the second embodiment, the distal exposed ends of the filaments 14, 16, 18, 20 may be insulated for either the atrial or ventricular placements described below.

In regard to the preferred types of introducer systems to be used with the above-described lead embodiments, either an external, lead body surrounding, introducer guiding, stiffening and filament restraining system or an internal lead body lumen stylet stiffening and guiding system with a filament restraint may be used. In the external introducer system, either a single sheath introducer or a double sheath introducer, having a coaxially nested pair of introducer sheaths, may be used. The choice may depend on the need for and ability of the introducer sheath(s) to assume curved shapes necessary to traverse the transvenous insertion route or effect the positioning of the helical pace/sense electrode 24 at a selected site within the right atrium or ventricle. For example, single sheath introducers having a mechanism for deflecting the tip may be used or double sheath introducers having a pre-curved inner introducer sheath and a straight outer introducer sheath may be used.

The type of lead connector employed at the proximal end of lead 10 may also affect the choice of introducer system used. Splittable introducer sheathes are necessary for lead bodies having conventional enlarged proximal end connectors for connection with the implantable cardioverter/ defibrillator pulse generator.

It should be noted that the application of torque down the length of the lead body 12 and lead extension 22 is necessary to rotate the helical pace/sense electrode 24 into and out of the myocardium. As described in the above-incorporated U.S Pat. No. 5,246,014, inner and outer introducer sheathes are used. The insulated junction 23 and/or the distal end of the inner introducer sheath 30 at opening 32 are shaped as a crank portion to be coupled together. Torque applied at the proximal end of inner introducer sheath 30 may be transmitted down the relatively stiff inner introducer sheath 30 and imparted via the crank portion to the helical pace/sense electrode 24. These torque enhancing features may be implemented in the preferred embodiments of the present invention. However, in animal implantation experiments conducted with embodiments of the present invention, it has not been found necessary to employ those disclosed torque enhancing features. With the wire filaments 14, 16, 18, 20 inside the lumen of the introducer sheath 30, the entire lead body 12 and lead extension 22 can be rotated from the proximal end connector to effect torque transmission to the helical electrode 24 to screw it into the myocardium.

Turning to FIGS. 9 and 10, they depict a preferred double splittable sheath introducer system 100 for providing the infusion and accommodating a cardioversion/defibrillation lead 10 of the present invention having a conventional, enlarged bipolar connector 82 formed at the proximal end thereof. The connector 82 is of the conventional, enlarged diameter type having a connector pin 86 electrically connected to the proximal end of pace/sense conductor 52, 62 and a connector ring 88 electrically connected to the proximal ends of cardioversion/defibrillation conductor 42 or the four wire filaments 14, 16, 18, 20.

The introducer system 100 comprises an inner, curved tip, splittable introducer 102 including introducer sheath 30 and an outer, straight tip, splittable introducer 110 having a splittable handle 112 of the conventional type. As shown in FIG. 10, the inner and outer introducers 102 and 110 are splittable in a peel away manner along their entire sheath lengths by grasping their handles 104 and 112 and pulling them apart as they are withdrawn from the patient's vein after the implantation is completed. Alternatively, the introducers 102 may be slittable by a slitting mechanism that fits over and snaps on (and off) the lead body and slits the introducer sheathes as they are withdrawn proximally in the manner of a percutaneous lead introducer known in the art. The latter mechanism may allow the use of a single catheter in lieu of the splittable introducer sheathes depicted.

In animal studies, it has been found that blood clots form at the end opening 32 within minutes of positioning the introducer sheath 30 and lead 10 within the heart chamber and prevent deployment of the wire filaments 14, 16, 18, 20. The blood clots cause the lead extension 22 and the wire filaments 14, 16, 18, 20 to stick together and to the lumen and interfere with the deployment described above. The introducer system choice is therefore also affected by the possible need to provide for infusion of a blood clot inhibiting agent, e.g. heparinarized saline, during the implantation procedure. In FIG. 9, the cardioversion/defibrillation lead 10 has been introduced with the helical electrode 24 and the wire filaments 14, 16, 18, 20 exposed distally. Infusion of heparinized saline is effected out of the end opening 32 of the inner introducer sheath 30. The fluid is infused in the lumen of the inner introducer sheath 30 and over the surface of the lead body 12. The handle assembly 104 of the inner splittable introducer is formed with a side port for attachment to a tube 106 and shut-off valve 108 which is in turn attached by a tube 114 to a source of the heparinized saline solution. The handle assembly 104 includes a hemostasis valve for sealing around the lead body 12 for preventing leakage proximally along the lead body. Such a side port and hemostasis valve body assembly in handle 104 is well known in the art and disclosed, for example, in U.S. Pat. No. 5,312,355, in conjunction with a splittable introducer.

In a further variation, an isodiametric connector of the type employed in temporary pacing leads, for example, may be substituted for the enlarged connector 82 of lead 10. Conventional inner and outer introducers may then be employed with luer locks and a side ported adaptor with a hemostasis valve within the inner introducer lumen for effecting the introduction of heparinarized saline without leakage proximally along the lead body 12.

In each case, a wire controlled, deflectable tip, single introducer having a valve and side port for infusion of heparinized saline may also be used. The single introducer may be splittable or not splittable, depending on the configuration of the lead connector 82.

In a further variation, the filaments 14, 16, 18, 20, the lead extension 22 the distal electrode 24 and the other structure at the distal end of the lead as well as the inner walls of the introducer sheath lumen they are fitted into may be coated with heparin. The coating may be sufficient by itself to prevent clotting or may augment the effectiveness of the applied heparinized saline solution.

Although not specifically illustrated, it will be understood that other introducer systems may be devised for introducing the leads 10 described above without an external introducer catheter system. The classic manner of introducing; a pacing and/or cardioversion/defibrillation lead employs a stiffening stylet advanced into a lead body lumen to stiffen it and provide steerability into the desired heart chamber location. Such a lumen extending the full length of the lead body and the lead extension 22 may be provided for receiving such a stylet. In such a case, the lead extension 22 may be enlarged to receive the stylet. The distal fixation mechanism may comprise flexible tines or a protection mechanism from which the helical pace/sense electrode is advanced during its fixation to the heart in a manner well known in the art. Hold down mechanisms may be provided for the filaments 14, 16, 18, 20 along the lead extension 22. Preferably, the filaments 14, 16, 18, 20 are held against the lead extension by a body compatible compound that dissolves in situ after a short time after fixation of the distal pace/sense electrode 24. Clot formation may have to be managed in this instance as well, and the filaments 14, 16, 18, 20 and the lead extension 22 may have to be coated or treated with the clot reducing heparin.

Upon release of the hold down mechanism or dissolution of the compound, the filament 14, 16, 18, 20 may spring free to assume their unrestrained curvature. In the first embodiment, the free ends of the filaments 14, 16, 18, 20 would then be advanced into the trabecular interstices or allowed to float freely, depending on the heart chamber.

Figure 11:
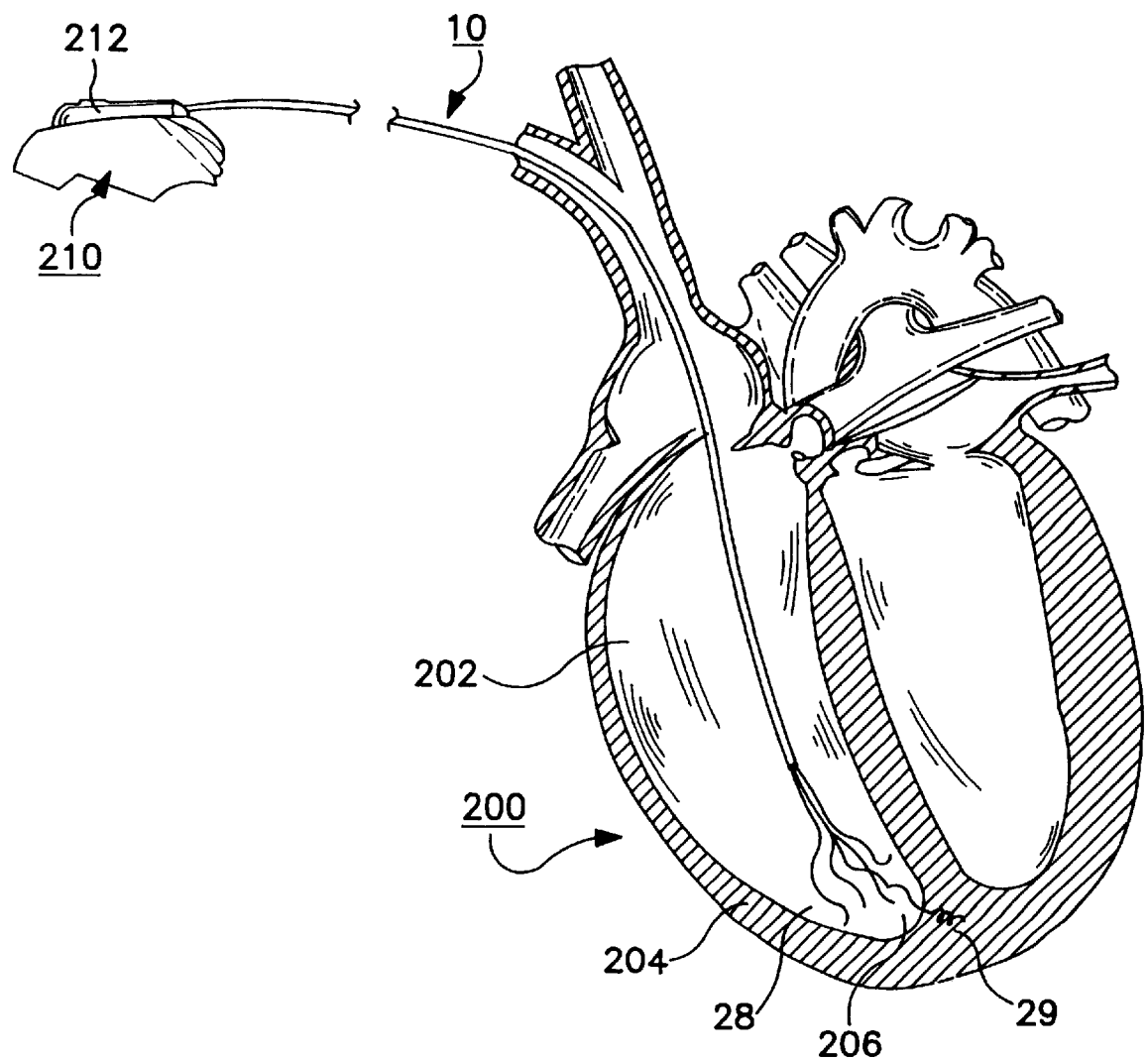
FIGS. 11 and 12 are schematic illustrations of the deployment of the pace/sense and cardioversion/defibrillation electrodes of the lead of FIGS. 1–3 in two locations in the right ventricular chamber.
Figure 12:
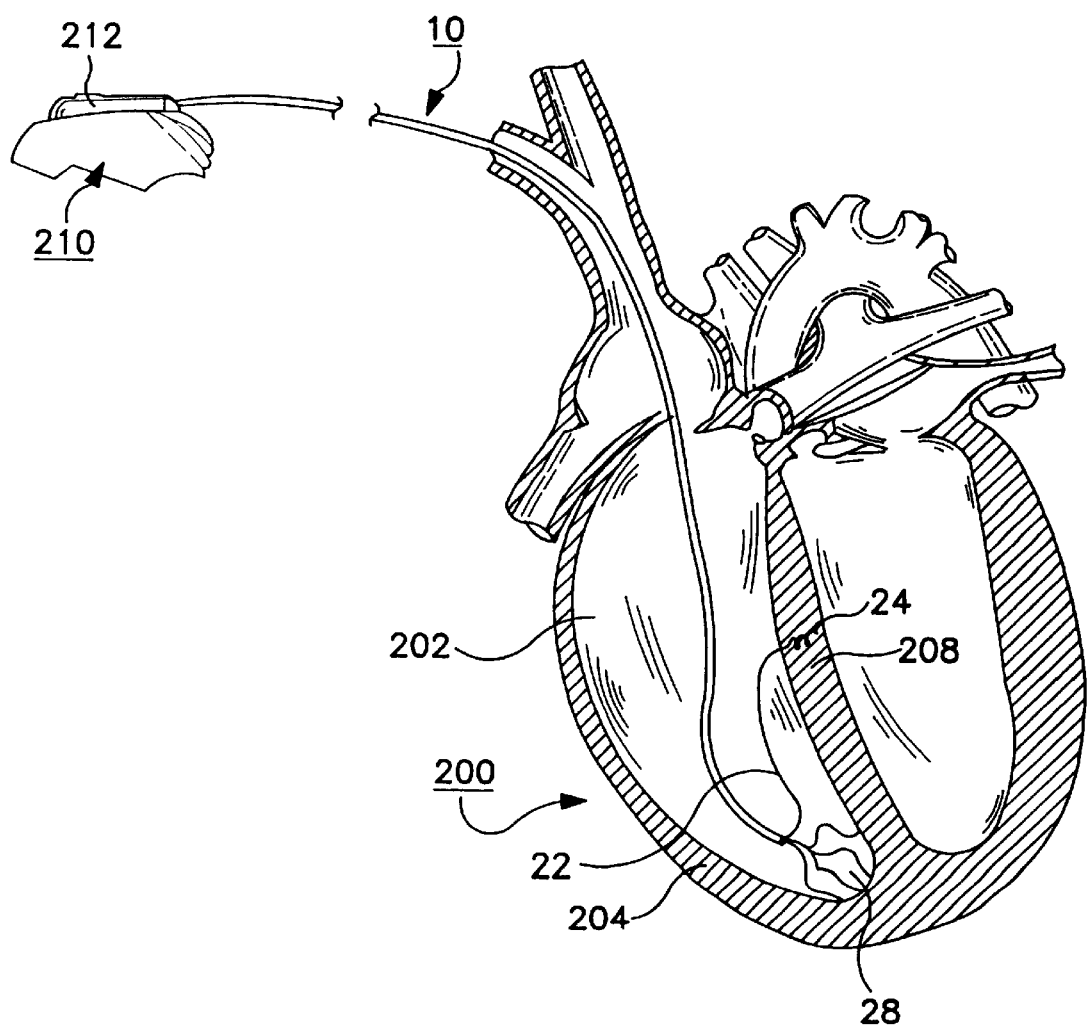
Figure 13:
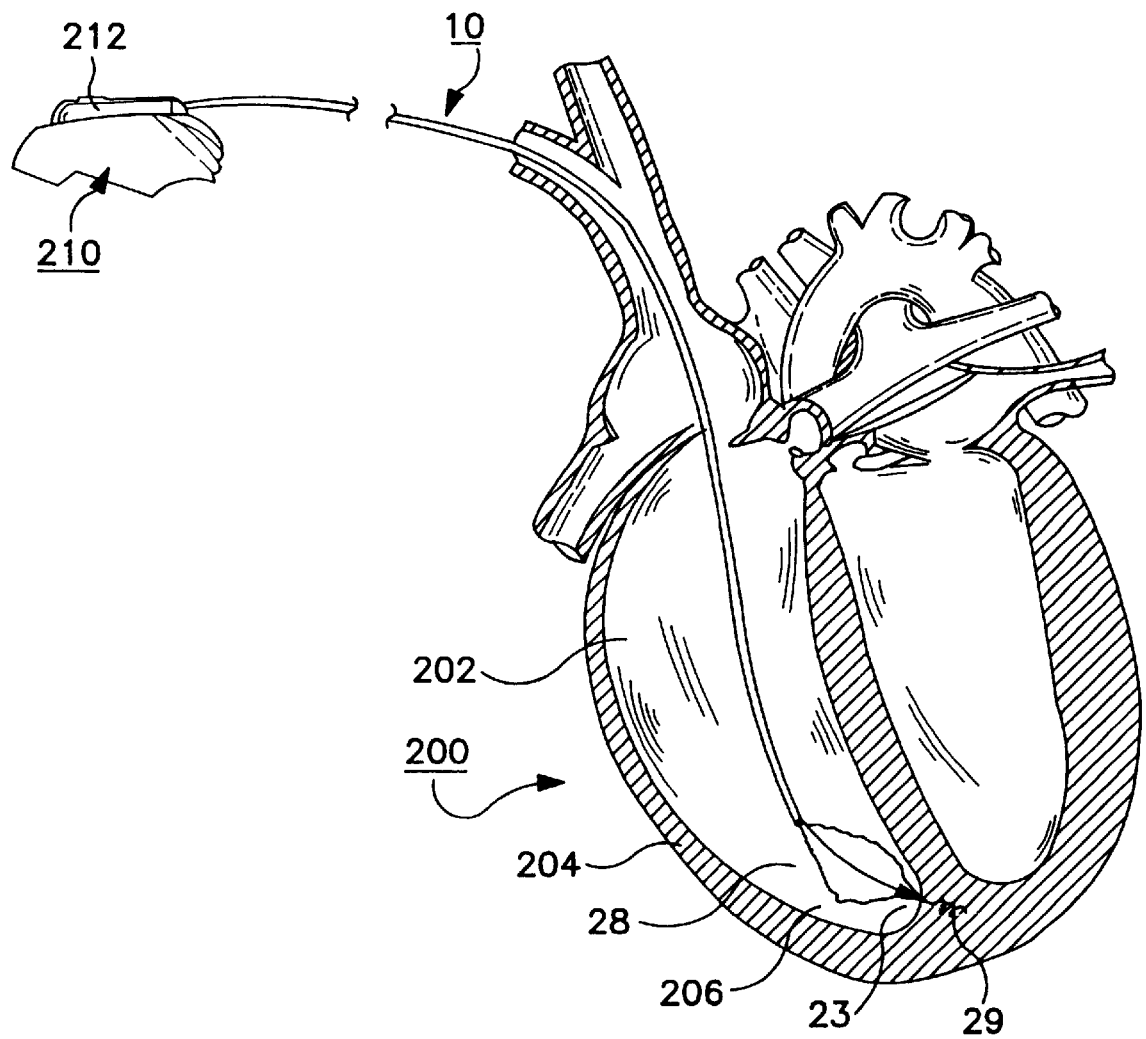
FIG. 13 is a schematic illustration of the deployment of the pace/sense and cardioversion/defibrillation electrodes of the lead of FIGS. 7–8 in the right ventricular chamber.

Turning to the positioning of the leads 10 of the present invention, FIGS. 11–13 depict the deployment of the pace/ sense electrode 24 and the cardioversion/defibrillation electrode 28 of the leads 10 of the embodiments of FIGS. 1–3 and 7–8, 16, 17 in the right ventricular chamber 202 of the heart 200. The lead connectors are attached to connector block 212 of the tachyarrhythmia implantable pulse generator 210 in a manner well known in the art after the lead 10 is transvenously introduced and the introducer system is removed.

In FIG. 11, the pace/sense electrode 24 has been screwed into the right ventricular apex, and the individual wire filaments 14, 16, 18, 20 of the cardioversion/defibrillation electrode 28 are deployed in interstices of the trabeculae in the region 206. The mass of trabeculae and the interstices are not specifically shown because of the difficulty of illustrating them. Generally, they are formed from the valve structure and extend down the length of the right ventricular chamber 202 into the apex 206. Depending on the shape of the right ventricular chamber 202 and the formation of the trabeculae, the individual wire filaments 14, 16, 18, 20 of the cardioversion/defibrillation electrode 28 are deployed as deeply into the apex as possible. The helical pace/sense electrode 24 is first imbedded as deeply as possible into the apex into contact with the myocardium before the individual wire filaments 14, 16, 18, 20 of the cardioversion/defibrillation electrodes 28 are deployed as described above, and the lead extension 22 bends as the filaments 14, 16, 18, 20 are extended. A similar process and positioning can take place if a tine fixation mechanism is employed for fixing pace/sense electrode 24 into contact with the patient's heart.

In FIG. 12, the pace/sense helical electrode 24 is first attached into the septum 24 closer to the outflow tract. The lead body 12 is then extended into the apex so that the individual wire filaments 14, 16, 18, 20 of the cardioversion/defibrillation electrode 28 are deployed as deeply into the apex as possible. This placement advantageously further separates the pace/sense electrode 24 from the cardioversion/defibrillation electrode 28. In addition, the pace/sense electrode 24 is placed higher in the conduction pathway extending down the ventricular septum 208 which ensures the isolation between the pace/sense electrode 24 and the wire filaments 14, 16, 18, 20 forming the cardioversion/defibrillation electrode 28. This separation minimizes the shock induced attenuation in the sensed EGM evident when the pace/sense electrode is closer to the cardioversion/defibrillation electrode.

Turning to FIG. 13, the lead 10 of the second embodiment is depicted in a deep ventricular apex position in an attempt to gain optimal cardioversion/defibrillation electrode positioning and dispersion while ensuring that the cardioversion/defibrillation electrode 28 does not short out with the pace/sense electrode 24 or any more proximal pace/sense ring electrode on lead extension 22.

Figure 14:
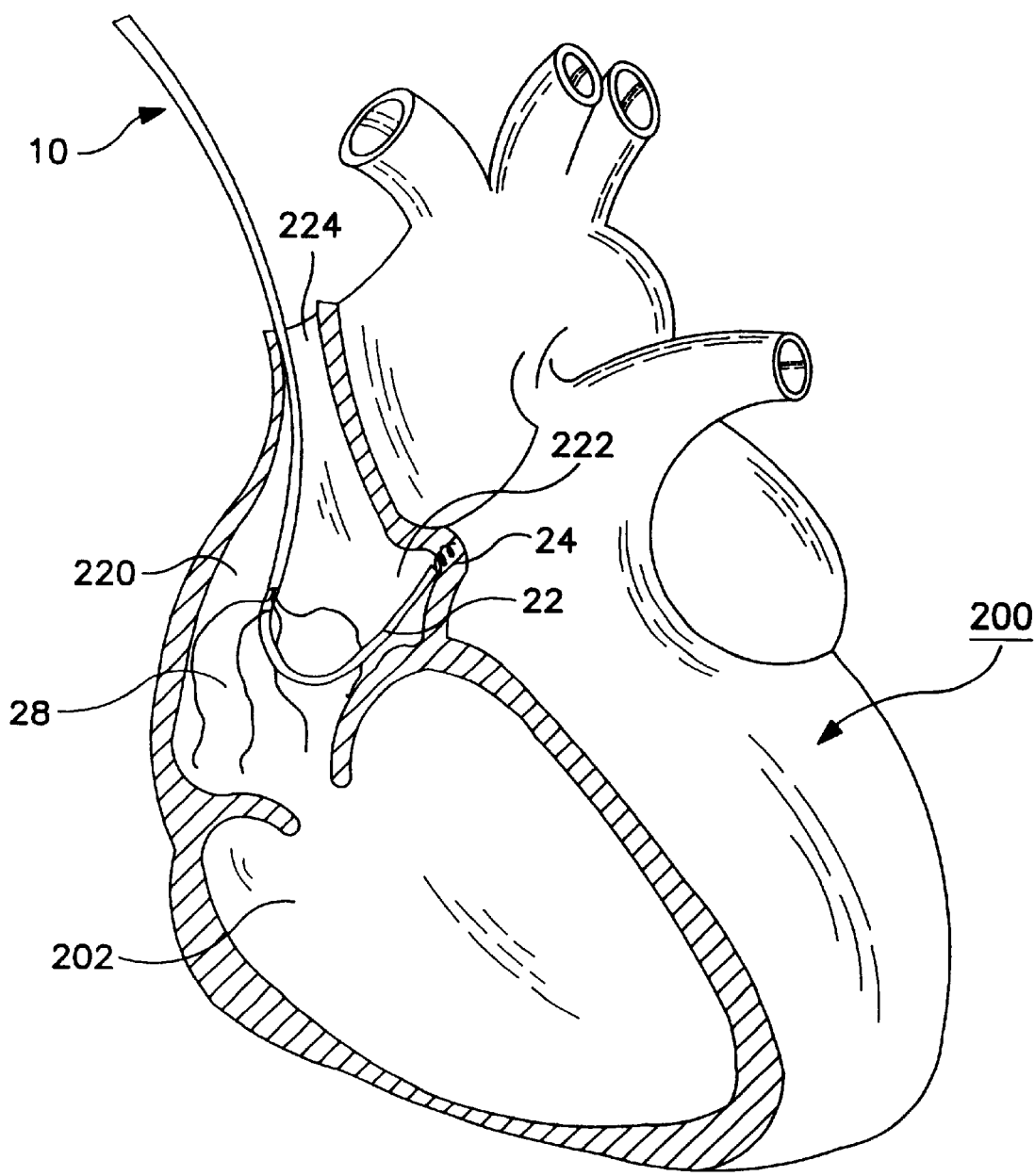
FIG. 14 is a schematic illustration of the deployment of the pace/sense and cardioversion/defibrillation electrodes of the lead of FIGS. 1–3 in the right atrial chamber.
Figure 15:
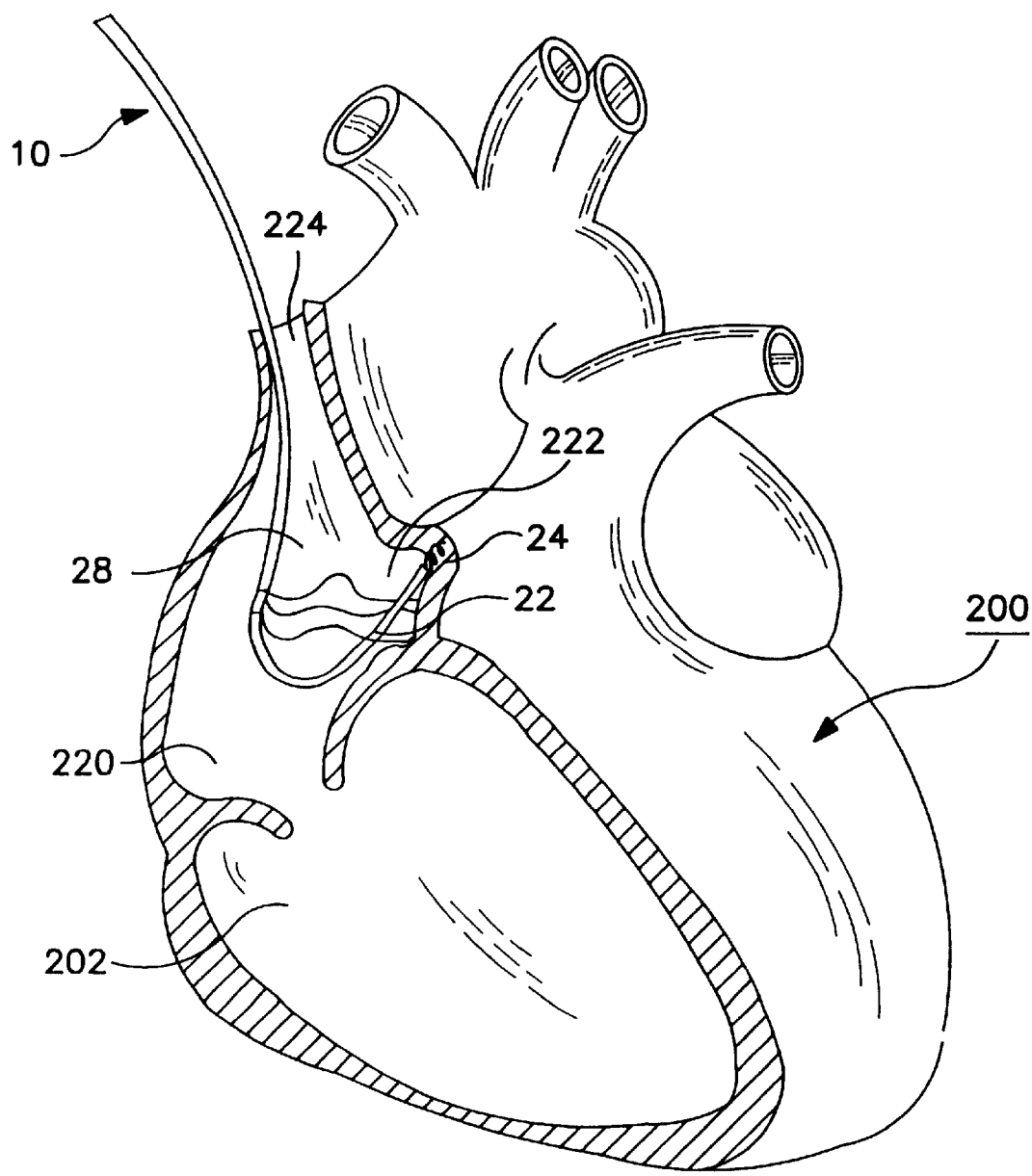
FIG. 15 is a schematic illustration of the deployment of the pace/sense and cardioversion/defibrillation electrodes of the lead of FIGS. 7–8 in the right atrial chamber.

Other locations of the lead systems of the present invention may also be employed. FIG. 14 depicts a placement of the cardioversion defibrillation lead 10 of the first embodiment of FIGS. 1–3 in the right atrium 220 of the heart 200. FIG. 15 depicts a placement of the cardioversion defibrillation lead 10 of the second embodiment of FIGS. 7–8 in the right atrium 220 of the heart 200. In both cases, the distal pace/sense helical electrode 24 is screwed into the relatively thick myocardium of the right atrial appendage 222. In FIG. 14, the free ends and lengths of the wire filaments forming cardioversion/defibrillation electrode 28 float in the blood in the right atrial chamber. In FIG. 15, the wire filaments forming cardioversion/defibrillation electrode 28 float in the blood but are restrained by the distal weak bonds thereof with the lead extension 22 described above in reference to FIGS. 7 and 8.

In all of these illustrations, the lengths of the distal lead extension 22 and the individual wire filaments 14, 16, 18, 20 of the cardioversion/defibrillation electrode 28 as well as their relative lengths and the position along lead body 12 where the individual wire filaments 14, 16, 18, 20 diverge from the lead body 12 or are attached back to the lead extension may be selected for the particular implantation site. Therefore, they may be longer or shorter than the lengths depicted and have relative relationships differing from those depicted. For example, the wire filaments 14, 16, 18, 20 of the cardioversion/defibrillation electrode 28 may be long enough to substantially traverse the length and width of the ventricular chamber as illustrated in FIGS. 11 and 12 or they may be positioned along lead body 12 to extend into the superior vena cava 224 of the heart 200 as illustrated in FIGS. 14 and 15.

Although the distal pace/sense electrode 24 is depicted as a helical screw-in electrode, it will be understood that it may take other forms and that the fixation may be accomplished by other means, e.g. soft pliant tines, flanges, penetrating hooks or the like.

Although a unipolar pace/sense electrode 24 and conductor in the distal extension 22 has been depicted, it will be understood that the invention may be practiced in bipolar pace/sense electrode configurations or that the defibrillation electrode 28 may be used as an indifferent pace/sense electrode. In the former case, a more distal ring electrode may be provided preferably in the second embodiment and distal to the insulated junction 23 to avoid contact with the filaments 14, 16, 18, 20.

In addition, it will be understood that a further cardioversion/defibrillation exposed coil wire electrode may be formed around the insulation along lead extension 22 and electrically connected in common with the filaments 14, 16, 18, 20 of any of the embodiments. Separate cardioversion/defibrillation structures may also be provided proximally along the lead body particularly for location in the superior vena cava 224 and/or right atrium.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

FIGS. 18 through 25 illustrate alternative embodiments of the leads according to the present invention, in which the small diameter coil or cable employed as defibrillation electrodes in conjunction with the leads illustrated in FIGS. 1–6 are employed in the context of a non-diverging, single electrode defibrillation lead. It has been determined by the inventors that even though these small diameter conductors provide an electrode which, for a given length, has substantially less actual surface area than typical prior art defibrillation electrodes, that surprisingly low defibrillation thresholds can be obtained using only a single length of the described small diameter coils or cables.

FIG. 18 illustrates a side, planned view of a third embodiment of a defibrillation lead according to the present invention, having a single defibrillation electrode taking the form of an exposed length of a small diameter coil 300. The lead body is takes the form of a single, non-diverging filament formed of two overlapping insulative sheaths including a proximal sheath 310 and a slidable distal sheath 306. Coil 300 extends from the distal end of sheath 306, along the central axis of the lead body. Coil 300 may, for example, take the form of a mono-filar or multi-filar close wound coil of wire having a diameter on the order of 0.004 inches, wound into a coil having a diameter preferably less than or equal to about two French, (i.e. about 0.030 inches in diameter or less), more preferably less than or equal to about one French (i.e., about 0.015 inches in diameter or less).

In the embodiment illustrated, the coil 300 takes the form of a mono-filar coil in which the distal tip 302 is sharpened and the distal turns 304 are pulled apart somewhat to provide for a fixation helix, which may be screwed into heart tissue. The exposed length of the coil 300 may be adjusted by movement of the outer insulative sheath 306, which may be moved proximally or distally over the electrode 300 to expose differing lengths of electrode coil. Preferably, sheath 306 is adjustable to allow for electrode coil 300 to have an exposed length of between 2 and 5 inches, to allow for adjustments of a lead to fit hearts of differing sizes. The outer sheath 306 is provided with a step up in diameter at 308, in order to allow it to surround a second insulative sheath 310 which terminates distally at a point proximal to shoulder 308 and extends proximally until connector assembly 312. Conductor 300 extends proximally within the lead body formed of sheaths 306 and 310 to the connector assembly 312, wherein it is connected to coupled to connector pin 314.

The location of insulative sheath 306, after adjustment, is fixed relative to the electrode coil 300 and insulative sheath 310 by means of one or more sutures 316, or alternatively, may be fixed in place by means of a compressive clamp or other mechanical mechanism. The point at which shoulder 308 comes in contact with the distal end of sheath 310 defines the most proximal position for sheath 306, while a point at which the overlap of the proximal end of sheath 306 with sheath 310 defines the distal-most location of sheath 306. The locations at which the cross-sections illustrated in FIGS. 19, 20, and 21, are also illustrated on FIG. 18 and are discussed below.

FIG. 19 illustrates a cross-section through the lead in a proximal portion of a lead, where slidable sheath 306 overlaps sheath 310. Coil 300 is illustrated as located within sheath 310 at this point.

FIG. 20 illustrates a cross-section through the lead at a point just proximal to the shoulder 308. Sheath 306 is illustrated in cross-section. The distal end surface of sheath 310 is illustrated, as well as coil 300.

FIG. 21 illustrates a cross-section of the lead at a point distal to the shoulder 308 of sheath 306. Surface of the shoulder 308 is visible, as is the cross-section through sheath 306, surrounding coil 300.

It should be noted that in the invention as illustrated, it is anticipated that body fluid may infiltrate into the lead body, entering through the proximal end of sheath 306. This is not believed to be a significant problem. However, in an alternate embodiment of the invention (not illustrated), it may also be desirable to provide a silicone rubber core through the center of conductor 300, to assist in minimizing both fluid infiltration and tissue ingrowth into coil 300.

FIGS. 22–25 illustrate a variant of the lead illustrated in FIGS. 18–21. In this embodiment of the invention, the connector assembly 412, connector pin 414, proximal insulative sheath 410 and distal insulative sheath 406 and sutures 416 correspond to connector assembly 312, connector pin 314, proximal sheath 310, distal sheath 306 and sutures 316 illustrated in FIG. 18. In this embodiment, a single cable 400, as described in conjunction with the leads illustrated in FIG. 6 above is substituted for the coiled conductor 300 in the lead illustrated in FIG. 18. A sharpened fixation helix 404 is located at its distal end, coupled to cable 400 by means of a crimp sleeve 402. Cable 400 may take the form of a seven filar cable described in conjunction with FIG. 6. Movement of distal sheath 406 relative to cable 400 to provide an electrode preferably having a length between two and five inches occurs in precisely the manner described above in conjunction with FIG. 18. The locations of the cross-sections through the lead illustrated in FIGS. 23, 24, and 25, are also shown in FIG. 22.

FIG. 23 illustrates a cross-section through the lead of FIG. 22 at a point proximal to the shoulder 408, at a point in which the distal sleeve 406 overlaps the proximal sheath 410. Cable 400 is visible in cross section.

FIG. 24 illustrates a cross-section through the lead illustrated in FIG. 22 at a point just proximal to the shoulder 408, with sheath 406 visible in cross-section and the end surface of proximal sheath 410 visible surrounding the cable 400.

FIG. 25 shows a cross-section through a body of the lead illustrated in FIG. 22 at a point distal to the shoulder 408 of distal sheath 406. The shoulder 408 is visible, as is a cross-section through the distal sheath, surrounding cable 400.

FIG. 26 illustrates the mechanism by which the leads illustrated in FIGS. 18 and 22 may be employed in conjunction with the stimulation of a human heart. While the specific lead illustrated is that shown in FIG. 22, it should be understood that the same basic mechanism applies to the lead illustrated in FIG. 18. The lead is first advanced by means of an introducer or guide catheter as described above in conjunction with the lead of FIG. 1 to a point where the fixation helix 404 can be screwed into the ventricle, at a desired location, which may be the apex or other location within the ventricle. Distal sheath 406 may then be adjusted relative to proximal sheath 410, while defibrillation thresholds are taken, to determine the ideal exposed length of cable 400. Upon determination of the ideal exposed length, sutures 416 are employed to stabilize the distal sheath 406 relative to the proximal sheath 410, and the connector assembly 412 is coupled to an implantable defibrillator or cardioverter 420. In conjunction with the lead illustrated in FIG. 22, the implanted defibrillator/cardioverter employs a second lead for pacing and sensing in the ventricle, comprising an elongated insulative lead body 422, carrying a ring electrode 424 and a helical, tip electrode 426 which may be screwed into the right ventricle. Alternative forms of pacing/sensing leads of types known to the art may, of course, be substituted.

FIG. 27 illustrates a side, plan view of an additional embodiment of a lead according to present invention. This lead may be embodied either as a stand-alone transvenous defibrillation lead or as part of the defibrillation leads illustrated in FIGS. 1–17. As illustrated in FIG. 27, the lead is embodied as a stand-alone defibrillation lead provided with a connector assembly 500 at its proximal end provided with a connector ring 502 and a connector pin 504. Sealing rings 506 and 508 are provided to seal the lead within the connector block of the associated implantable defibrillator, in a conventional fashion. An elongated, non-diverging lead body 510 extends distally from the connector assembly 500 and takes the form of a bi-lumen tube of polyurethane, silicone, or other similar biocompatible plastic. A defibrillation coil electrode 512 is visible located along the distal portion of the lead, and a helical electrode 514 is shown located at the distal most extremity of the lead. Electrode 514 is coupled to connector pin 504 by means of a coiled or cabled conductor located within a first lumen extending longitudinally within lead body 510. Coil electrode 512 is a continuation of a coiled conductor located in a second lumen within the lead body 510, extending proximally to and coupled to connector ring 502. Overall, it is desirable that the lead have a diameter in the vicinity of electrode 512 of 4 French or less, which may be accomplished in the context of a bipolar lead, by employing the structure and method of manufacture illustrated in FIG. 28.

FIG. 28 illustrates a side, cutaway view through the lead of FIG. 27, in the region of electrode coil 512. In this view, it can be seen that a lead body 510 is provided with two internal lumens 516 and 518, which extend side by side along the length of lead body 510. A first multi-filar coiled conductor 520 is shown in the first lumen 518, conductor 520 extends distally to fixation helix 514 and extends proximally to connector pin 504. A cabled conductor or mono-filar coil conductor may also be substituted for conductor 520. In this view it can be seen that coil electrode 512 takes the form of an elongated multi-filar coil having a relatively short, distally extending portion 512a wound at a smaller diameter and a relatively longer, proximal extending portion 512b, also wound at a smaller diameter than exhibited by the electrode coil 512 along the portion of the lead over which electrode 512 is exposed.

Rather than employing sleeves, crimps, swages or other relatively complicated interconnected mechanisms, the lead according to the present invention is fabricated according to a methodology produces a structure which allows for a substantial reduction in the overall cross-section size of the lead. Electrode coil 512 is fabricated as an expanded diameter portion of an elongated multi-filar coil, which has a length appropriate to extend from the expanded diameter portion which will serve as the coil electrode, all the way proximally to the connector assembly. This elongated, reduced diameter portion of the coil is inserted into the first lumen 516 through an aperture such as a slot or slit 522, cut in the outer wall of the lumen. The coil is then slid proximally until the increased diameter portion of the coil 512 reaches the slit or slot 522. The expanded diameter portion of the coil may either then be wound around the lead body 510. The expanded diameter portion of electrode coil 512 is then compressed longitudinally, to form a close wound coil so that the distal end of the relatively shorter reduced diameter portion of the coil 512a may be inserted into a second slot 524. Upon re-expansion of the coil, the reduced diameter portion 512a moves distally, securing the distal end of the coil 512 relative to the lead body 510. The portion of the lead lumen 516 adjacent the slots 522 and 524 may then be back filled with adhesive 526, both to seal the lumen 516 against ingressive fluids and to provide a strain relief at the ends of the exposed portions of the electrode coil 512. For sake of simplicity, the back fill 526 is illustrated in the vicinity of slot 522 but should be understood to also be present in the vaccinate of slot 524.

An alternative construction technique may be to slide the reduced diameter portion 512b of the coil 512 proximally until the expanded diameter portion of the coil reaches the distal end of the lead body 510, thereafter inserting the distal end of the lead body into the expanded diameter portion of the coil 512, and thereafter. moving the coil proximally along the lead body until the expanded diameter portion of the coil reaches the slot 522, with the rest of the assembly procedure as described above.

By means of this simplified structure and assembly mechanism, it is not necessary to provide for the additional cross-sectional area generally required by prior art interconnection mechanisms for connecting a conductor to an exposed defibrillation electrode coil on a defibrillation lead. One particular proposed embodiment of the lead as illustrated employs an elongated lead body 510 fabricated of a bi-lumen polyurethane tube fabricated of a polyurethane having a relatively high durameter, such as 55D or higher durometer polyurethane, and employs a quadri-filar defibrillation coil electrode 512 manufactured of silver cored MP35N or tantalum wire, coated with platinum, having an overall outer diameter in the expanded diameter portion of the coil approximately 4 French or less. Preferably, the exposed, expanded portion of the coil 512 has a length in the vicinity of two inches, however other lengths may also be employed. Although not illustrated, a slidable sheath as used in the leads of FIGS. 18 and 22 may optionally be employed to adjust the exposed length of the coil electrode.

A lead according to this embodiment of this invention may be employed as a stand-alone lead as illustrated, or may be substituted, for example, for the lead extension portion 22 of the lead illustrated in FIG. 1. In this case, an additional defibrillation electrode surface would be added, which may also be employed in the context of an integrated bipolar sensing system, in which sensing of cardiac depolarizations and delivery of cardiac pacing pulses may occur between helical electrode 514 and defibrillation electrode coil 512 or alternatively, pacing and sensing may be accomplished between electrode 514 and the housing of the implantable defibrillator or other electrodes. Such an alternative embodiment is illustrated in FIG. 30, described below.

FIG. 29 illustrates a lead as illustrated in FIG. 27, as implanted in the human heart. Implantation of the lead may be accomplished using the same procedure as described above in conjunction with the implantation of the leads described in FIGS. 1–17, by advancing the lead down an introducer or guide catheter, screwing helical electrode 514 into the tissue of the ventricle, removing the guide catheter or extended introducer, and connecting the connector assembly 500 to an implantable defibrillator 530. All other labeled elements correspond to identically numbered elements illustrated in FIG. 27.

FIG. 29 illustrates the embodiment described above in which the lead illustrated in FIG. 1 is incorporated in a lead otherwise as illustrated in FIG. 1. In this case, the extension 22 of the lead of FIG. 1 is substituted with a structure corresponding to the distal portion of the lead illustrated in FIG. 27. As illustrated, the lead is coupled to an implantable defibrillator 540. Lead body 12 and electrodes 14, 16, 18, and 20 correspond to identically labeled components illustrated in FIG. 1, and introduction of the lead is accomplished using the same mechanism as discussed in conjunction with introduction of the lead illustrated in FIG. 1. While not illustrated, it should be understood that the distal portion of the lead illustrated in FIG. 27 may also be employed in a lead otherwise as illustrated in FIGS. 8 et seq., in a corresponding fashion.

The small diameter defibrillation leads illustrated in FIGS. 18, 22 and 27 are all shown as provided with helical fixation members, typically taking the form of electrodes, as a mechanism for anchoring the tips of the leads in the heart. It should be understood that the embodiments of the inventions illustrated in these figures may also alternatively be practiced in conjunction with the use of one or more pliant tines, or other fixation mechanisms located at the distal ends of the lead bodies.

What is claimed is:

1. An implantable electrical lead, comprising:
   an elongated insulative lead body having a proximal end and a distal end;

a defibrillation electrode comprising a plurality of conductive filaments extending distally from the lead body at a first point between the proximal and distal ends of the lead body and having free distal ends unattached to the lead body;

a cardiac pacing electrode located at the distal end of the lead body; provided with means for fixing the pacing electrode to heart tissue;

first conductor means coupled to the pacing electrode and extending proximally within the lead body, for coupling the pacing electrode to an implantable cardioverter or defibrillator; and second conductor means coupled to the defibrillation electrode and extending proximally within the lead body, for coupling the defibrillation electrode to an implantable cardioverter or defibrillator.

2. A lead according to claim 1 wherein the second conductor means comprises a plurality of elongated conductors extending along the lead body, each coupled to a single one of the conductive filaments.

3. A lead according to claim 2, wherein the lead body comprises a plurality of longitudinally extending internal lumens each having a distal opening and internal diameter sufficient to admit a said conductive filament, and each of the plurality of elongated conductors is slidably mounted in the lead body in a said lumen, whereby proximal traction applied to a proximal end of one of the plurality of elongated conductors retracts the conductive filament to which it is attached into the lead body.

4. A lead according to claim 3 wherein each of the plurality of elongated conductors is mounted in a separate one of said lumens within the lead body.

5. A lead according to claim 1 wherein the conductive filaments are biased to spring outward of said lead body when not restrained.

6. A lead according to claim 5 wherein the conductive filaments are biased to assume different curved configurations when not restrained.

7. A lead according to claim 1 wherein the free ends of the conductive filaments terminate proximal to the pacing electrode.

8. An implantable electrical lead, comprising:

an elongated insulative lead body having a proximal end and a distal end;

a defibrillation electrode comprising a plurality of conductive filament extending distally from the lead body at a first point between the proximal and distal ends of the lead body and having distal ends removably attached to the lead body at a second point distal to the first point, the distal ends removable by means of proximal traction applied to the conductive filaments;

a cardiac pacing electrode located at the distal end of the lead body; provided with means for fixing the pacing electrode to heart tissue;

first conductor means coupled to the pacing electrode and extending proximally within the lead body, for coupling the pacing electrode to an implantable cardioverter or defibrillator; and second conductor means coupled to the defibrillation electrode and extending proximally within the lead body, for coupling the defibrillation electrode to an implantable cardioverter or defibrillator, the second conductor means mounted slidably within the lead body whereby proximal traction applied to the second conductor means causes removal of the distal ends of the conductive filaments from the lead body.

9. A lead according to claim 8 wherein the second conductor means comprises a plurality of elongated conductors extending along the lead body, each coupled to a single one of the conductive filaments.

10. A lead according to claim 9, wherein the lead body comprises a plurality of longitudinally extending internal lumens each having a distal opening and internal diameter sufficient to admit a said conductive filament, and each of the plurality of elongated conductors is slidably mounted in the lead body in a said lumen, whereby proximal traction applied to a proximal end of one of the plurality of elongated conductors retracts the conductive filament to which it is attached into the lead body.

11. A lead according to claim 10 wherein each of the plurality of elongated conductors is mounted in a separate one of said lumens within the lead body.

12. A lead according to claim 8 wherein the conductive filaments are biased to spring outward of said lead body when not restrained.

13. A lead according to claim 8 wherein the distal ends of the conductive filaments terminate proximal to the pacing electrode.

* * * * *

UNITED STATES PATENT AND TRADEMARK OFFICE
CERTIFICATE OF CORRECTION

PATENT NO. : 6,178,355 B1
DATED : January 23, 2001
INVENTOR(S) : Williams et al.

It is certified that error appears in the above-identified patent and that said Letters Patent is hereby corrected as shown below:

<u>Title page,</u>
Item [75] Inventors, please delete "Xiaoyi Min, Plymouth"

<u>Column 21, claim 8,</u>
Line 47, "filament" should read -- filaments --

Signed and Sealed this

Thirteenth Day of November, 2001

*Attest:*

*Attesting Officer*

NICHOLAS P. GODICI
*Acting Director of the United States Patent and Trademark Office*